(12) United States Patent
Leung et al.

(10) Patent No.: US 10,792,110 B2
(45) Date of Patent: Oct. 6, 2020

(54) SYSTEMS AND METHODS FOR DETERMINING INTRAOPERATIVE SPINAL ORIENTATION

(71) Applicant: 7D SURGICAL INC., Toronto (CA)

(72) Inventors: Michael K. K. Leung, Markham (CA); Adrian Mariampillai, Toronto (CA); Beau Anthony Standish, Toronto (CA); Peter Siegler, Toronto (CA); Victor X. D. Yang, North York (CA)

(73) Assignee: 7D SURGICAL INC., Toronto, Ontario (CA)

( * ) Notice: Subject to any disclaimer, the term of this patent is extended or adjusted under 35 U.S.C. 154(b) by 92 days.

(21) Appl. No.: 16/314,809

(22) PCT Filed: Jul. 4, 2017

(86) PCT No.: PCT/CA2017/050806
§ 371 (c)(1),
(2) Date: Jan. 2, 2019

(87) PCT Pub. No.: WO2018/006167
PCT Pub. Date: Jan. 11, 2018

(65) Prior Publication Data
US 2019/0307513 A1    Oct. 10, 2019

Related U.S. Application Data

(60) Provisional application No. 62/358,124, filed on Jul. 4, 2016.

(51) Int. Cl.
*A61B 34/20* (2016.01)
*A61B 17/70* (2006.01)
*A61B 34/10* (2016.01)

(52) U.S. Cl.
CPC .............. *A61B 34/20* (2016.02); *A61B 17/70* (2013.01); *A61B 17/7074* (2013.01);
(Continued)

(58) Field of Classification Search
CPC ......... A61B 6/032; A61B 5/055; A61B 34/20; A61B 2034/107; A61B 34/10;
(Continued)

(56) References Cited

U.S. PATENT DOCUMENTS 9,119,670 B2    9/2015   Yang et al.
2008/0063301 A1  3/2008   Bogoni et al.
(Continued)

FOREIGN PATENT DOCUMENTS

WO    2011078933 A1    6/2011
WO    2015074158 A1    5/2015
(Continued)

OTHER PUBLICATIONS

International Search Report for the parent PCT application PCT/CA2017/050806, dated Nov. 10, 2017.
(Continued)

*Primary Examiner* — Joseph D Burgess
(74) *Attorney, Agent, or Firm* — Hill & Schumacher

(57) ABSTRACT

Systems and methods are disclosed whereby a surface detection system is employed to obtain intraoperative surface data characterizing an exposed surface of the spine. In some embodiments, this intraoperative surface data is registered to segmented surface data obtained from volumetric data of the spine in order to assess the intraoperative orientation of the spine and provide feedback associated with the intraoperative orientation of the spine. The feedback may characterize the intraoperative spinal orientation as a change relative to the preoperative orientation.

34 Claims, 19 Drawing Sheets

(52) U.S. Cl.
 CPC ... *A61B 2034/105* (2016.02); *A61B 2034/107* (2016.02); *A61B 2034/2065* (2016.02); *A61B 2034/2074* (2016.02)

(58) Field of Classification Search
 CPC ...... A61B 2090/364; A61B 2034/2065; A61B 2090/363; A61B 2090/378; A61B 6/5235; A61B 2090/3983; A61B 2090/3735; A61B 2090/376; A61B 2090/3762
 See application file for complete search history.

(56) References Cited

U.S. PATENT DOCUMENTS

| | | | |
|---|---|---|---|
| 2010/0054525 A1 | 3/2010 | Gong et al. | |
| 2016/0030131 A1 | 2/2016 | Yang et al. | |
| 2016/0191887 A1* | 6/2016 | Casas | H04N 13/279 348/47 |

FOREIGN PATENT DOCUMENTS

| | | |
|---|---|---|
| WO | 2016026053 A1 | 2/2016 |
| WO | 2016044934 A1 | 3/2016 |
| WO | 2017219149 A1 | 12/2017 |

OTHER PUBLICATIONS

Herring, Jeannette and Benoit Dawant, "Automatic Lumbar Vertebral Identification Using Surface-Based Registration", Journal of Biomedical Informatics 34, 74-87 (2001).

* cited by examiner

| Level ID | Δ Axial Angle (°) | Δ Sagittal Angle (°) | Δ Displacement (mm) |
|---|---|---|---|
| 1 | 6.0 | 7.1 | 9.1 |
| 2 | 10.5 | 8.9 | 24.2 |
| 3 | 9.7 | 15.3 | 54.2 |
| 4 | 8..8 | 11.1 | 25.4 |
| 5 | 7.1 | 7.2 | 13.2 |

| Level ID | Δ Angle (°) |
|---|---|
| 1 | 4.8 |
| 2 | 8.1 |
| 3 | 13.4 |
| 4 | 10.7 |
| 5 | 5.9 |

SYSTEMS AND METHODS FOR DETERMINING INTRAOPERATIVE SPINAL ORIENTATION

CROSS-REFERENCE TO RELATED APPLICATION

This application is a National Phase application claiming the benefit of the international PCT Patent Application No. PCT/CA2017/050806, filed on Jul. 4, 2017, in English, which claims priority to U.S. Provisional Application No. 62/358,124, titled "SYSTEMS AND METHODS FOR DETERMINING INTRAOPERATIVE SPINAL ORIENTATION" and filed on Jul. 4, 2016, the entire contents of which are incorporated herein by reference.

BACKGROUND

This disclosure relates generally to surgical systems and methods, and more particularly to systems and methods for spinal surgery.

The vertebral column is composed of a series of articulated overlapping segments. The function of the vertebral column is to support a person while standing, balance the individual in the presence of gravity, and enable locomotion and other useful movements. Deformities of the spine include conditions such as idiopathic adolescent scoliosis, congenital scoliosis, post-traumatic deformities, and other adult spinal deformity including post-infective kyphosis.

Spinal deformity correction surgery utilizes devices (primarily screws and rods) to fixate levels of the spine in a corrected or compensating position to restore normal posture. Surgical navigation can be used to aid the positioning of screws and other implants within the spine but provides relatively little feedback on the intraoperative orientation of the spine.

Traditionally, intraoperative CT and/or fluoroscopy can be used to assess the orientation of the spine, but these systems are expensive, require the use of large amounts of ionizing radiation, and are cumbersome to use.

SUMMARY

Systems and methods are disclosed whereby a surface detection system is employed to obtain intraoperative surface data characterizing an exposed surface of the spine. In some embodiments, this intraoperative surface data is registered to segmented surface data obtained from volumetric data of the spine in order to assess the intraoperative orientation of the spine and provide feedback associated with the intraoperative orientation of the spine. The feedback may characterize the intraoperative spinal orientation as a change relative to the preoperative orientation. Alternatively, the feedback may consist of displaying the intraoperative spinal orientation by updating the volumetric data.

Accordingly, in a first aspect, there is provided a method of determining an intraoperative orientation of a spine, the method comprising:

obtaining volumetric image data pertaining to a spine;
processing the volumetric image data to generate multi-level surface data characterizing a bone surface of the spine;
processing the multi-level surface data to generate segmented surface data on a per-level basis for each level of a plurality of spinal levels;
intraoperatively detecting, with a surface detection subsystem, intraoperative surface data characterizing surface regions associated with each spinal level of the plurality of spinal levels;
for each spinal level of the plurality of spinal levels:
employing volumetric fiducial points associated with said each spinal level and corresponding intraoperative fiducial points associated with said each spinal level to perform an initial registration between the segmented surface data associated with said each spinal level and the intraoperative surface data, and subsequently performing a surface-to-surface registration between the segmented surface data associated with said each spinal level and the intraoperative surface data, thereby obtaining a registration transform associated with said each spinal level; and
employing the registration transforms associated with the plurality of spinal levels to generate measures associated with an intraoperative spinal orientation, and providing feedback based on the measures.

In another aspect, there is provided a system for determining an intraoperative orientation of a spine, the system comprising:

a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:

processing volumetric image data pertaining to a spine to generate multi-level surface data characterizing a bone surface of the spine;
processing the multi-level surface data to generate segmented surface data on a per-level basis for each level of a plurality of spinal levels;
controlling said surface detection subsystem to intraoperatively detect intraoperative surface data characterizing surface regions associated with each spinal level of the plurality of spinal levels;
for each spinal level of the plurality of spinal levels:
employing volumetric fiducial points associated with said each spinal level and corresponding intraoperative fiducial points associated with said each spinal level to perform an initial registration between the segmented surface data associated with said each spinal level and the intraoperative surface data, and subsequently performing a surface-to-surface registration between the segmented surface data associated with said each spinal level and the intraoperative surface data, thereby obtaining a registration transform associated with said each spinal level; and
employing the registration transforms associated with the plurality of spinal levels to generate measures associated with an intraoperative spinal orientation, and providing feedback based on the measures.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1:
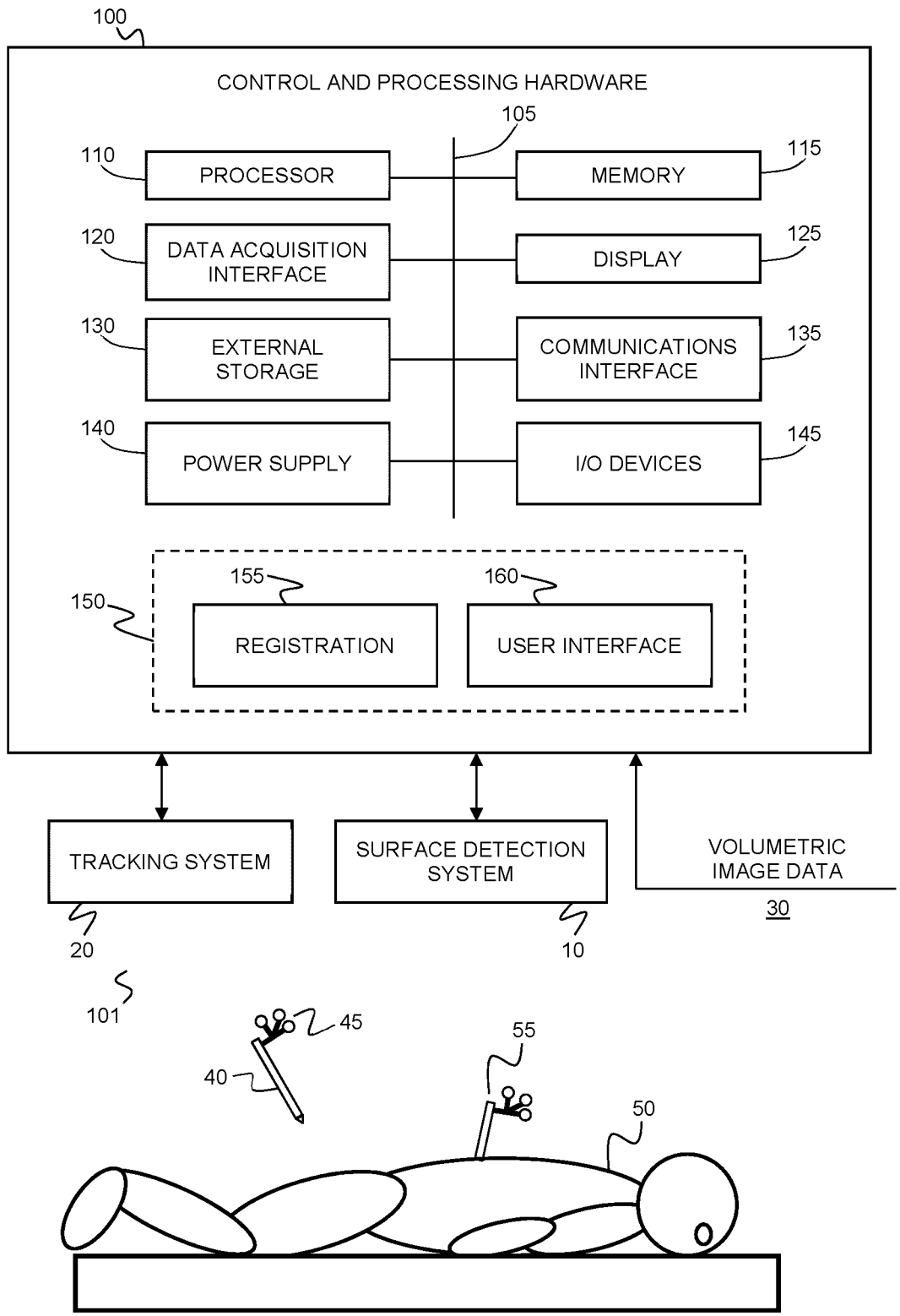
FIG. 1 shows an example system for determining the intraoperative orientation of the spine and generating feedback associated therewith.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

As used herein, the term "spinal orientation" refers to the six degrees of freedom in which spinal levels can move relative to other spinal levels. Alternatively, it is also referred to as the "orientation of the spine". As used herein, the six degrees of freedom of each individual spinal level is referred to by the term "position" for the translational component, and the term "orientation" is used for the rotational component.

Various example embodiments of the present disclosure provide systems and methods for determining information pertaining to the orientation of the spine during (or after) performing a spinal procedure. During a spinal procedure, at least two spinal levels are typically exposed intraoperatively. These spinal levels are henceforth referred to as intraoperative spinal levels. The intraoperative spinal orientation, which may change due to a spinal intervention (such as the use of screws and rods to correct for a spinal deformity or pathology), may be difficult to visualize, since only a small subset of the spine is typically exposed, and since the surgical field of view is typically complicated by the presence of tissue and blood, thus presenting potential difficulty to the surgeon in assessing the effect of an intervention on the resulting spinal orientation. As a result, intraoperative X-rays are frequently required, which allows the surgeon to visualize anatomical structures much deeper than the surgical exposure for spinal level confirmation. This increases the surgical time, and exposes the operating room staff and patient to ionizing radiation. It is readily apparent that the consequences of the incorrect execution of a surgical plan, as a result of an inappropriate surgical correction, can have significant negative consequences for patient and the surgeon.

Various aspects of the present disclosure address this problem by providing solutions that employ a surface detection system to obtain intraoperative surface data characterizing the exposed surface of the spine. This intraoperative surface data may be compared with segmented surface data obtained from volumetric data of the spine in order to assess the intraoperative orientation of the spine and provide feedback associated with the intraoperative orientation of the spine. As discussed below, the feedback may characterize the intraoperative spinal orientation as a change relative to the preoperative orientation. The feedback may be relative to a spinal orientation obtained via a volumetric imaging modality at an earlier phase of the procedure. The feedback may also be relative to another instance in time during the surgery of a previous intraoperative spinal orientation. The term "intraoperative", as used herein, refers to an event that occurs during a surgical procedure or after the conclusion of a phase of a surgical procedure. For example, an intraoperative measurement involving the surface topography of an exposed potion of the spine may occur any time that the spine is exposed, such as during an interventional phase of a surgical spinal procedure, and after the interventional phase, but prior to closing the surgical incision.

In one example embodiment, segmented surface data is obtained from the volumetric image data, such that the segmented surface data corresponds to a pre-selected spinal segment that is expected to be exposed intraoperatively during the surgical procedure. The segmented surface data from the pre-selected spinal level, and additional segmented surface data from other spinal levels, is registered to the intraoperative surface data, achieving efficient registration, on a per-level basis, and thereby facilitating an assessment of the intraoperative spinal orientation (in absolute terms, or relative to the spinal orientation that existed when the volumetric image data was obtained). As described in detail below, various example methods disclosed herein may employ the determination of a set of inter-level registration transforms between adjacent levels in the volumetric frame of reference, in order to assist in the registration between segmented surface data of the various levels and the intraoperative surface data, thereby potentially improving the efficiency and accuracy of the inferred intraoperative spinal orientation.

Referring now to FIG. 1, an example system is shown for determining an intraoperative orientation of the spine based on intraoperative surface detection. The system includes a surface detection system 10 that is operably interfaced with control and processing hardware 100. The surface detection system 10 may be any suitable system for detecting, measuring, imaging, or otherwise determining the surface topography of one or more objects (such as, but not limited to, a region of an exposed spine of a patient 50) using optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

The example system may also include a tracking system 20, which may be employed to track the position and orientation of one or more medical instruments 40. The medical instrument 40 is shown having fiducial markers 45 attached thereto, and passive or active signals emitted from the fiducial markers 45 are detected by the tracking system 20 (e.g. a stereoscopic tracking system employing two tracking cameras). In an alternative example embodiment, the position and orientation of a medical instrument may be tracked via a surface detection subsystem 10, such as a structured light detection system, that is employed to detect the surface profile of at least a portion of the medical instrument, or structure attached thereto, and to determine the position and orientation of the medical instrument via comparison of the detected surface profile with a known surface profile.

As also shown in FIG. 1, a tracked reference frame 55 (e.g. a clamp with fiducial markers provided thereon or attached thereto) may be attached to the patient and may be tracked by the tracking system 20. Such a tracked reference frame 55 may be employed for image guided surgeries.

FIG. 1 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment, and is not intended to be limited to the components shown. Furthermore, one or more components of the control and processing hardware 100 may be provided as an external component that is interfaced to a processing device. For example, as shown in the figure, one or both of the surface detection system 10 and the tracking system 20 may be included as a component of control and processing hardware 100, or may be provided as one or more external devices.

Although only one of each component is illustrated in FIG. 1, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, that include executable instructions, which when executed by the one or more processors 110, causes the system to perform one or more methods described in the present disclosure. Such instructions may be stored, for example, in memory 115 and/or other internal storage. In particular, in the example embodiment shown, registration module 155 includes executable instructions for registering segmented surface data (obtained from the volumetric image data 30) with intraoperative surface data that is obtained using the surface detection system 10, and for determining measures and feedback associated with an intraoperative orientation of the spine (e.g. relative to the spinal orientation in the volumetric image data). The registration module 155 may also be employed for computing inter-level registration transforms between adjacent levels in the volumetric frame of reference, as per some of the example embodiments described below. The navigation user interface module 160 includes executable instructions for displaying a user interface for performing, for example, image-guided surgical procedures.

Various example embodiments of the present disclosure that pertain the intraoperative determination of spinal orientation employ the registration of segmented surface data (obtained by processing volumetric image data of the spine) with intraoperative surface data (intraoperatively obtained using a surface detection system; also known as a surface topography detection system or surface profile detection system). The volumetric image data may be obtained pre-operatively, using, for example, imaging modalities such as, but not limited to, computed tomography (CT) and magnetic resonance imaging (MRI). Alternatively, the volumetric image data may be obtained intraoperatively, for example, using intraoperative CT or intraoperative MRI.

As described above, in some example embodiments, the spinal orientation, as determined during or after a spinal procedure involving an exposed portion of the spine, may be determined by performing registration between segmented surface data (obtained from volumetric image data) and intraoperative surface data, and employing the resulting registration transforms to generate measures, and/or a visualization, associated with the intraoperative orientation of the spine, where the measures and/or visualization may, in some example embodiments, pertain to the change in the spinal orientation relative to the spinal orientation in the volumetric image data, or relative to another instance in time during the surgical procedure.

Figure 4A:
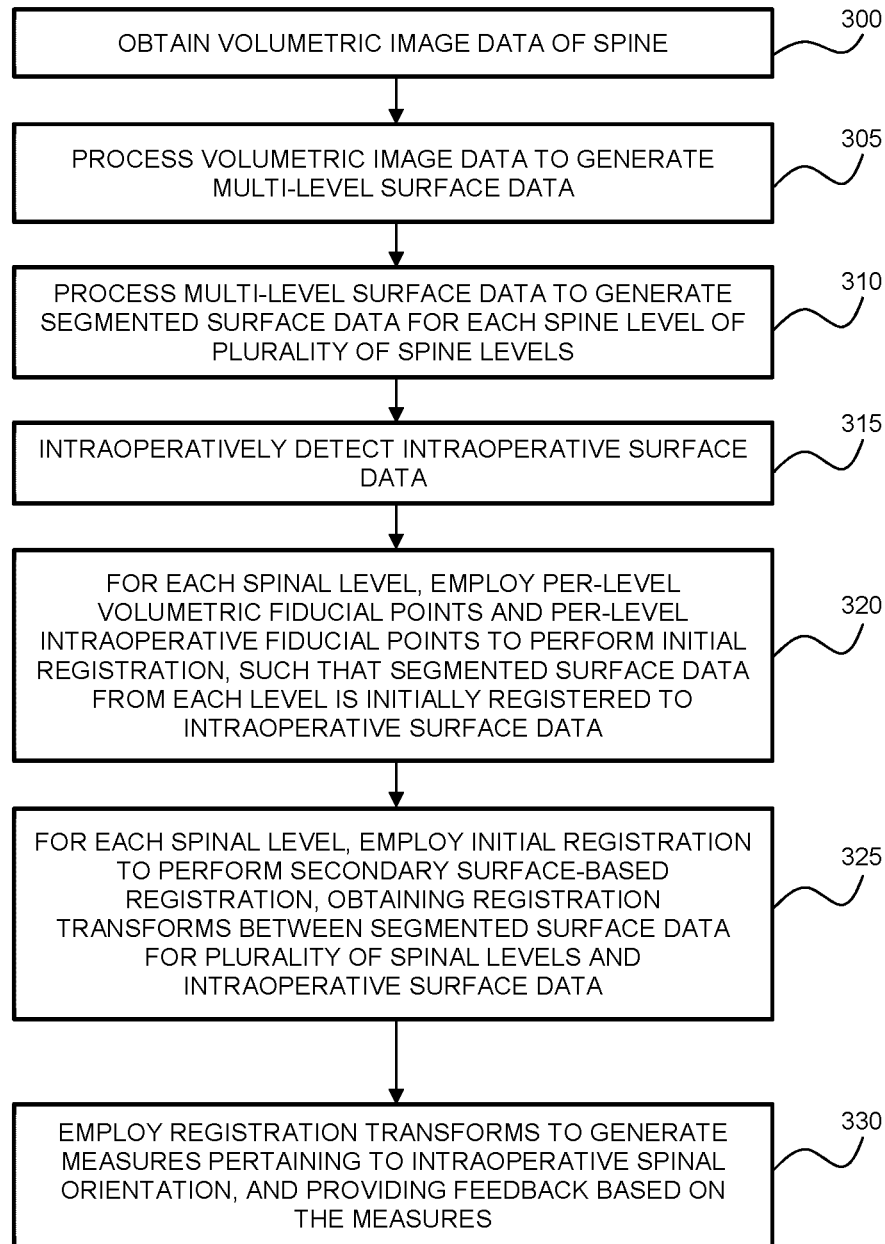
FIG. 4A is a flow chart illustrating an example method of generating feedback associated with the intraoperative orientation of the spine based on intraoperative surface detection.

Referring now to FIG. 4A, an example method is illustrated for determining the intraoperative orientation of a spine (at least a portion of the spine that includes the intraoperatively exposed levels) based on intraoperatively acquired spine surface topography data. In step 300, volumetric image data of the spine is obtained, as described above. Multi-level surface data is then obtained by processing the volumetric image data, as shown at 305, such that the multi-level surface data includes at least a plurality of spinal levels that are expected to be exposed during the surgical procedure.

Figure 2A:
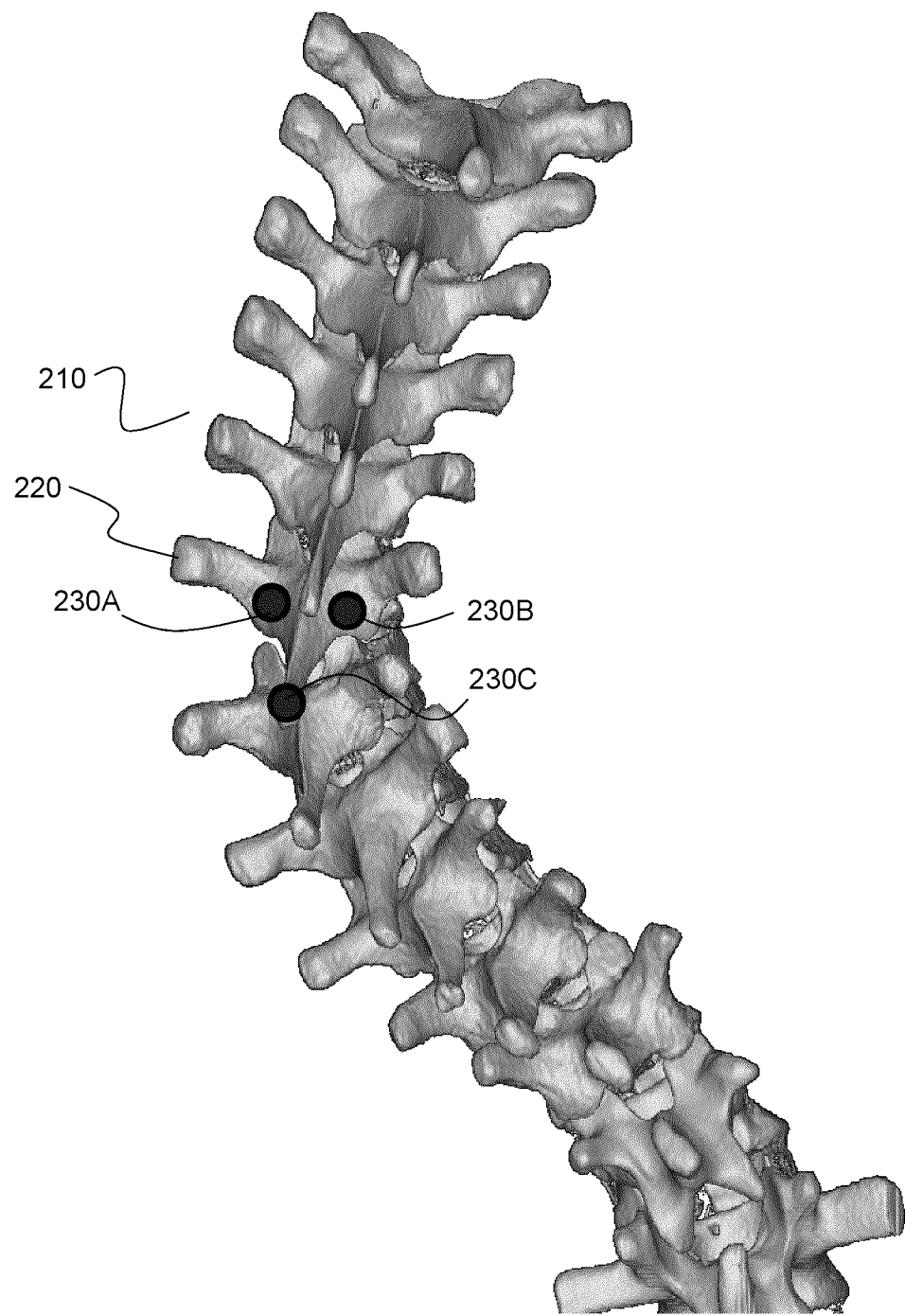
FIG. 2A illustrates an example multi-level surface generated by thresholding volumetric image data of the spine to determine a surface corresponding to bone, showing the pre-selected spinal level that is expected to correspond to a selected intraoperatively exposed spinal level. The figure also shows three volumetric fiducial points located at the pre-selected spinal level.

An example a multi-level surface 210 is shown in FIG. 2A. In the multi-level surface image 210 of the spine, many volumetric spinal levels can be seen, potentially allowing a clear determination of the identity (i.e. level number) of a given volumetric spinal level. This multi-level surface 210, characterized by associated multi-level surface data, resides in the volumetric frame of reference that is associated with the volumetric image data. The multi-level surface data may be generated according to a wide variety of methods. One example involves the selection of a bone threshold and generating an isosurface using the marching cubes algorithm from the volumetric image data. Another example is to construct an isocontour from each 2D slice of a volumetric image data based on a bone threshold, and stitching the slices together into a 3D surface.

Figure 2B:
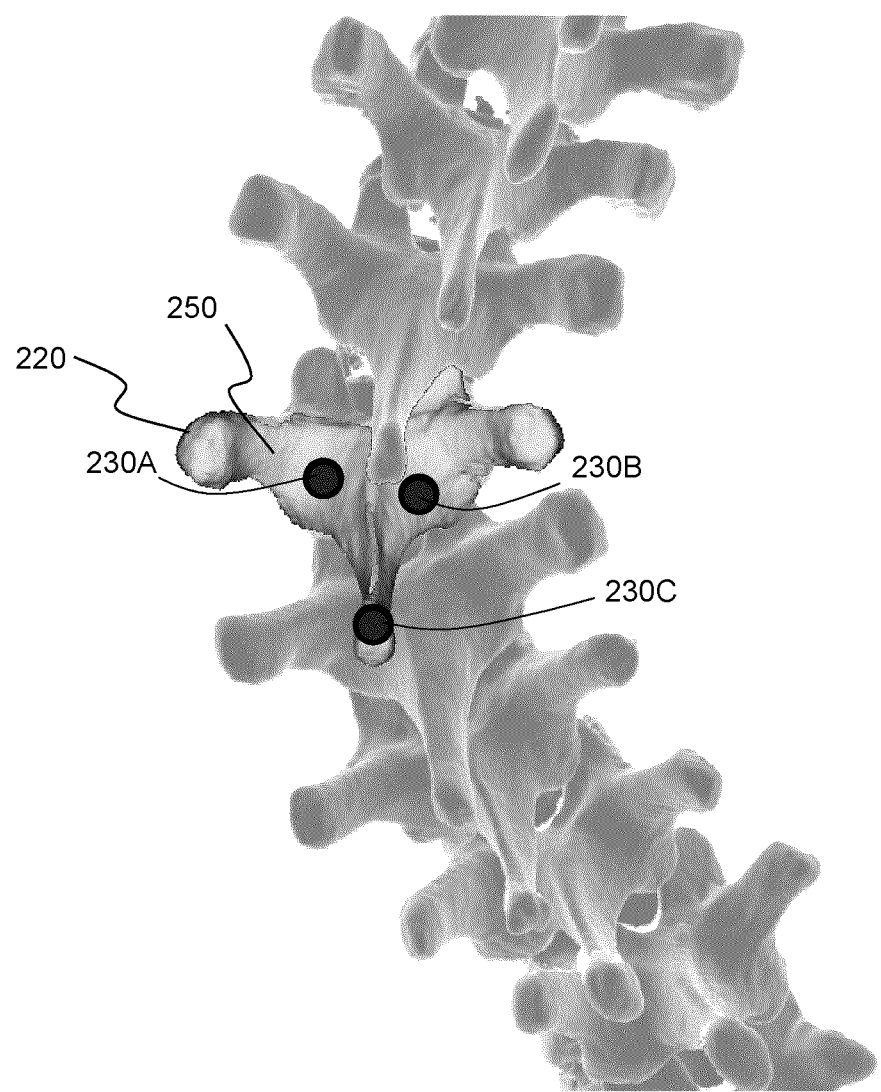
FIG. 2B illustrates an example segmented surface, obtained by segmenting the multi-level surface of FIG. 2A at the pre-selected spinal level (as identified by the volumetric fiducial points).

The multi-level surface data 210 is then processed to generate the segmented surface data associated with each level of the plurality of spinal levels, as shown at step 310 of FIG. 4A. An example of segmented surface data 250 is shown in FIG. 2B, where the segmented surface data 250 corresponds to level 220 of FIG. 2A. The segmentation of the multi-level surface data to obtain the segmented surface data may be performed according to any suitable method. One or more of the volumetric fiducial points, such as volumetric fiducial points 230A-C in FIG. 2A, may be employed to initiate surface segmentation of a given level. The volumetric fiducial points associated with a given spinal level may be provided via manual input (e.g. as input received from a user or operator), or automatically generated, as described in further detail below.

Non-limiting examples of surface segmentation methods include non-template-based methods and methods which utilize anatomical shape models. Non-template-based methods can utilize geometrical properties, such as connectivity, surface normals, and curvatures to determine the boundary of the segmented region, or statistical properties, such as variance from nearby neighboring points on the surface. Methods based on anatomical shape models can utilize a pre-computed atlas of vertebra as a template to perform the segmentation. Both classes of methods can also be used in combination. In all these methods, one or more volumetric fiducial points can serve as a seed point to initialize the segmentation process. Alternatively, for segmentation methods which are fully automatic and operate on the entire volumetric data (which are usually based on anatomical atlases), one or more volumetric fiducials can be used to tag the level(s) of interest.

Figure 2C:
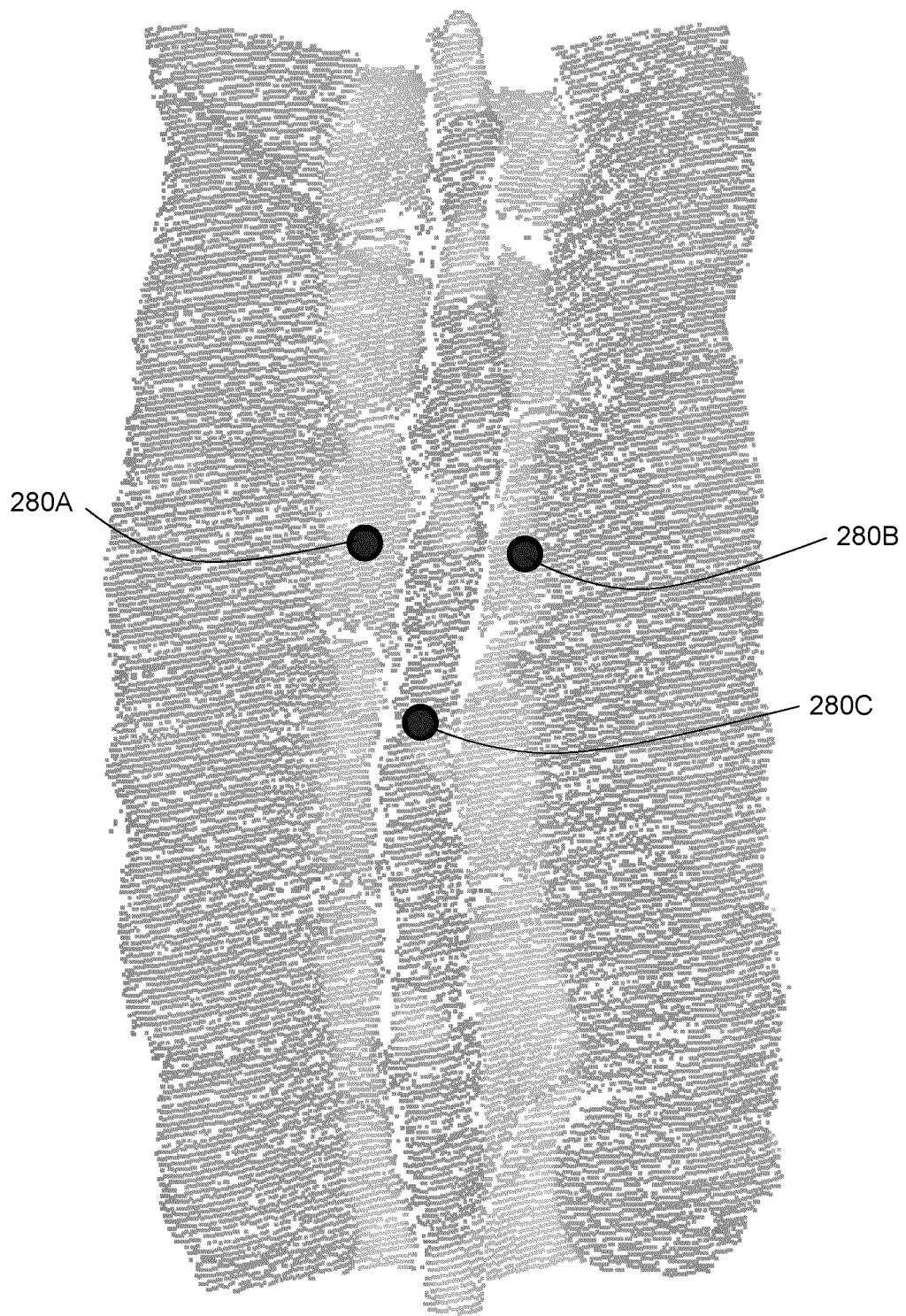
FIG. 2C illustrates an intraoperative surface detected using a surface detection system, showing several intraoperatively exposed spinal levels. Three intraoperative fiducial points, corresponding to the volumetric fiducial points, identify the intraoperatively selected spinal segment that is believed to correspond to the pre-selected spinal level in the volumetric frame of reference.

As shown in step 315 of FIG. 4A, intraoperative surface data is obtained using a surface detection system such as, but not limited to, a structured light detection system. FIG. 2C shows an example of intraoperative surface data detected using a structured light detection system. In contrast to the multi-level surface data 210 shown in FIG. 2A, the intraoperative surface data only has partial bone exposed. The intraoperative surface data may be obtained in a single scan or image, such that a single intraoperative surface topography dataset is obtained including multiple spinal levels in the field of view. Alternatively, the intraoperative surface data may be obtained using two or more surface topography measurements, such that each measurement pertains to one or more spinal level.

Having generated the per-level segmented surface data corresponding to the plurality of spinal levels in the volumetric frame of reference, the segmented surface data for each level may be registered to the intraoperative surface data of the exposed spine, as shown in steps 320 and 325. This registration may be performed as an initial registration based on correspondence, at each level, between per-level volumetric fiducial points and respective per-level intraoperative fiducial points, as shown at step 320 of FIG. 4A. The per-level intraoperative fiducial points associated with a given spinal level may be provided via manual input (e.g. as input received from a user or operator), or automatically generated, as described in further detail below.

After generating the initial registration for each spinal level, a surface-to-surface registration may then be performed for each level, between the per-level segmented surface data and the intraoperative surface data, thereby obtaining a set of per-level registration transforms, as shown at step 325 of FIG. 4A. The registration transforms respectively map, for each level, the segmented surface in the volumetric frame of reference to the intraoperative surface data. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

The registration transforms may be processed to determine measures pertaining to the relative positions and orientations of the spinal levels, as shown at step 330, and these measures may be employed to generate intraoperative feedback. Such measures may provide the spatial relationships among spinal levels within the intraoperative frame of reference, and also the intraoperative changes in the positions and orientations of the spinal levels relative to the spinal level positions and orientations in the volumetric image data. These measures may be employed to generate feedback pertaining to the intraoperative orientation of the spine. As used herein, "intraoperative orientation" may refer to the positions of the spinal levels, and/or the orientations of the spinal levels.

For example, the intraoperative spinal level position and orientation of the exposed spinal levels may be determined by identifying a set of volumetric level positions and orientations in the volumetric frame of reference, each volumetric level position and orientation identifying a position and orientation pertaining to a given spinal level in the volumetric frame of reference, and then employing the volumetric level position and orientation and the per-level registration transforms to determine an intraoperative set of intraoperative level position and orientation of the spinal levels. The set of intraoperative level positions and orientations may be employed to generate a visualization of the intraoperative locations of the spinal levels.

The registration transforms may also be employed to determine measures of the change in orientation of each level from the volumetric frame of reference to the intraoperative frame of reference (e.g. a set of angles prescribing the angular change of the spinal level). If the orientations and positions of the spinal levels in the volumetric frame of reference are known (e.g. as defined by a per-level point and normal vector), then the registration transforms can be employed to determine the intraoperative per-level positions and orientations.

The volumetric level positions and orientations may be determined by several different methods, non-limiting examples of which are provided below. It will be understood that many different methods may be employed to determine a suitable reference location of a spinal level.

In one example implementation, a volumetric level position may be determined by processing the segmented surface data in order to determine the center of mass of the fiducial set for the spinal level. In some cases, the segmented surface data may be generated such that each point in the segmented surface data has a normal vector associated therewith. In such a case, normal vectors may be obtained by determining, for each volumetric fiducial point, an associated closest point in the segmented surface data, and then obtaining a corresponding normal vector for each closest point. The resulting normal vectors may then be averaged to provide a mean orientation to define the vector associated with the orientation of the level. If the segmented surface data does not include an associated normal vector for a given closest point, then a vector associated with the closest point can be determined by employing a set of neighboring points to determine a local tangential plane, thereby obtaining a normal vector associated with the local tangential plane. This method is particularly useful if each of the fiducial set contains fiducials which are selected in a consistent manner from level to level. For example, a typical fiducial set pattern would consist of one fiducial selected on the center left lamina, center right lamina and the center of the spinous process. A second fiducial set pattern might consist of the left inferior facet joint, left superior facet joint, right inferior facet joint, right superior facet joint, inferior tip of spinous process, superior tip of spinous process.

In a second example implementation, each of the fiducial sets may be used as seeds to initiate a region growing process to segment a region of each level in a similar manner as the segmentation of multi-level surface data into segmented surface data. The points within the segmented regions may then be used to calculate a mean position for each level to define the point. Similarly, the mean orientation of each level may be calculated by averaging the normal associated with each of the points contained within the segmented regions. This method may outperform the method described above when fiducials are not consistently selected from level to level.

Figure 8:
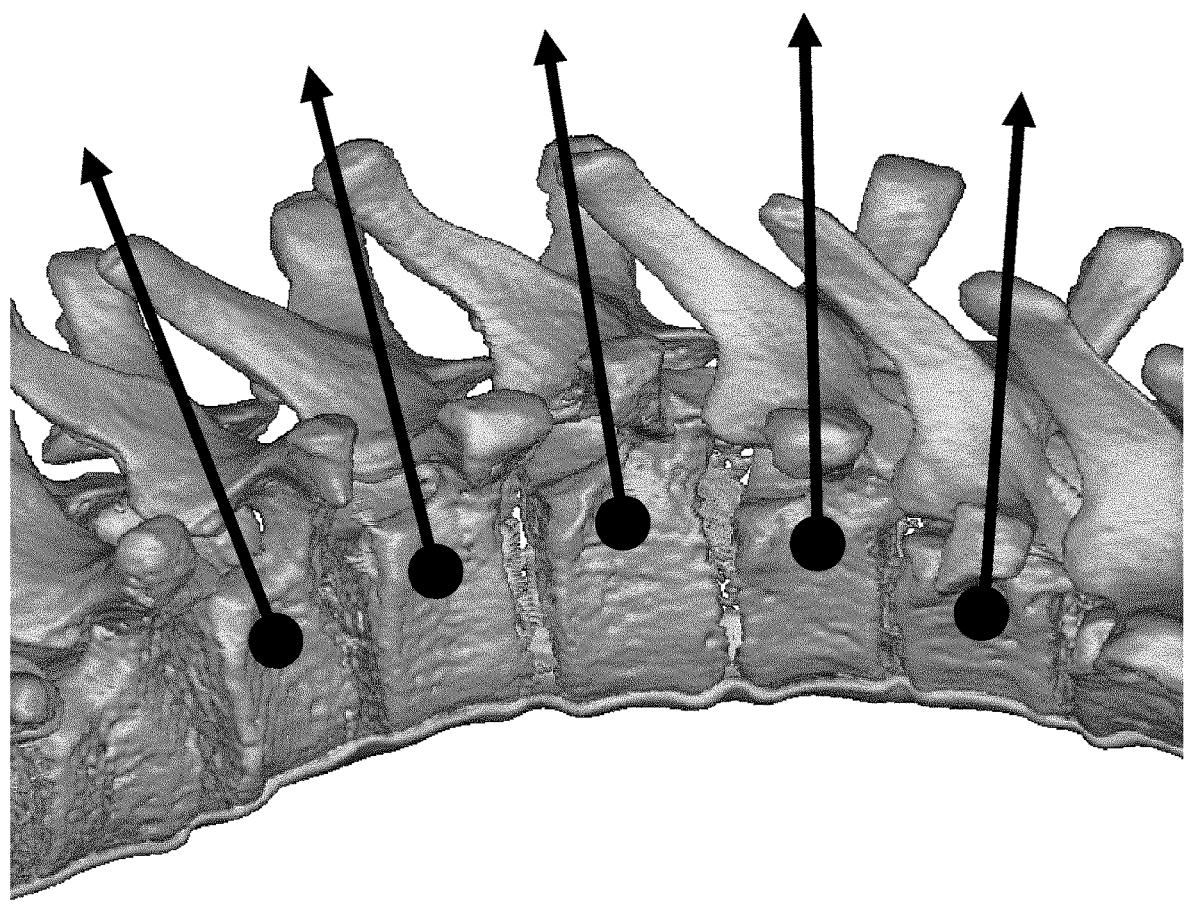
FIG. 8 shows an example graphical user interface, wherein the position and orientation of spinal levels from the volumetric data can be defined and adjusted by the user by dragging an orientation vector and moving a point.

In a third example implementation, a graphical user interface can be employed to receive input from a user selecting a suitable per-level reference location. For example, a user may provide input to select (e.g. drag) a point. The input may also permit adjustment of an orientation vector overlaid onto a 3D rendering of the volumetric surface data to define this information. An example graphical user interface to do this is shown in FIG. 8.

Figure 9A:
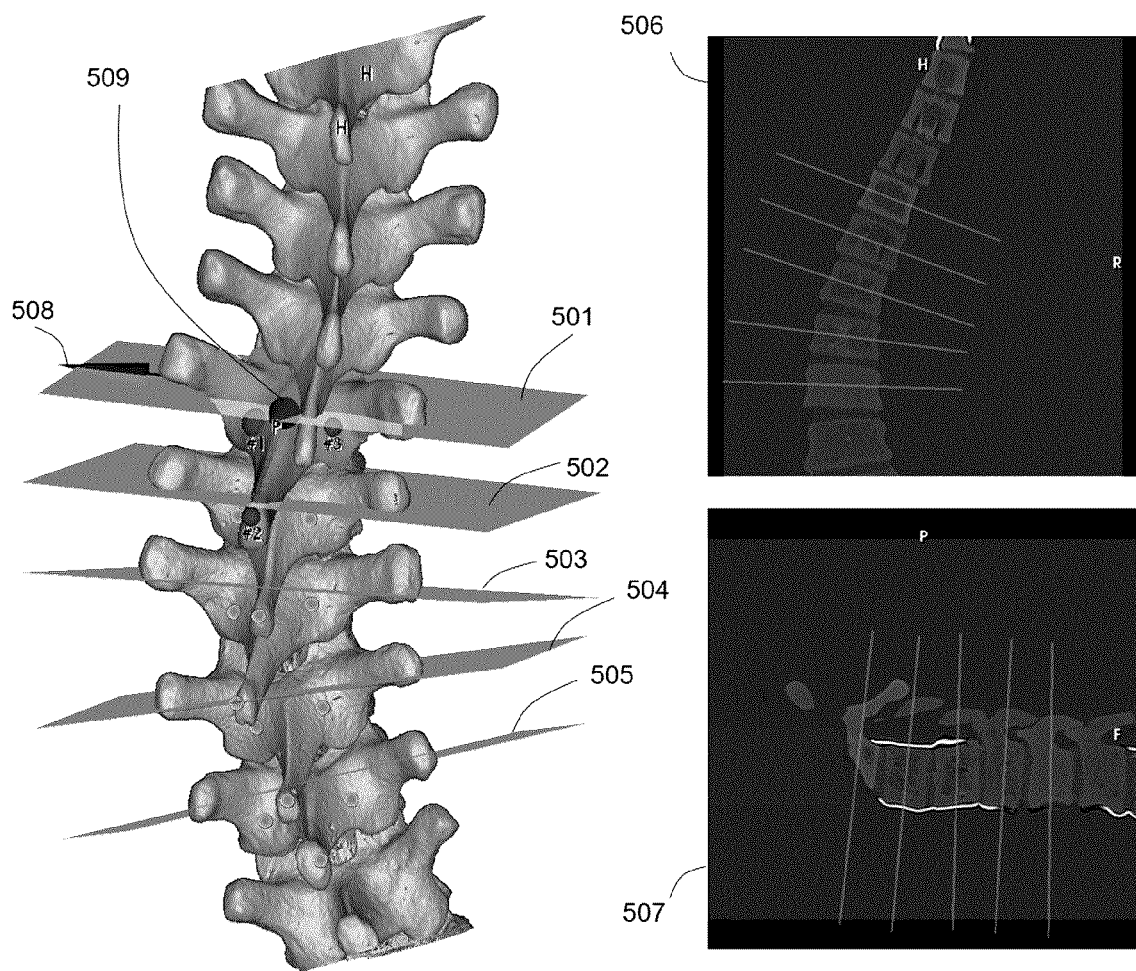
FIG. 9A shows an example graphical user interface, wherein the position and orientation of spinal levels from the volumetric data can be defined and adjusted by the user by adjusting oriented planes centered at each spinal level.
Figure 9B:
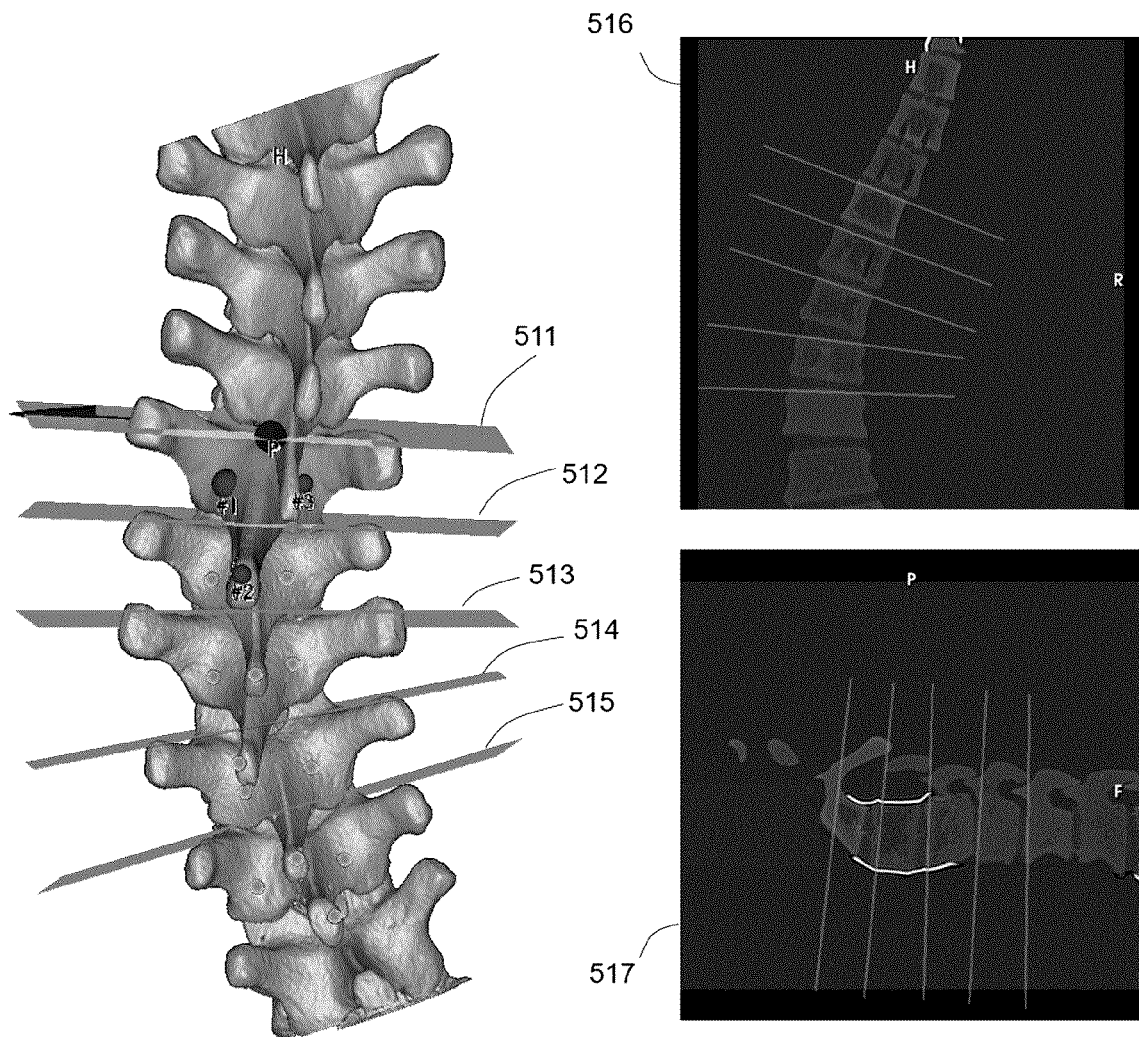
FIG. 9B shows an example graphical user interface as shown in FIG. 9A, where the end plates of each spinal level are used as a visual feature to place the oriented planes.

In a fourth example implementation, a plane can be shown in a graphical user interface, enabling the user to manipulate the plane such that it describes the orientation of the spinal level. FIG. 9A shows an example of such a user interface. A plane 501 that describes the orientation of a spinal level is shown. To assist the user in manipulating the planes, indicator arrows suggesting a particular direction of the spinal level can be shown. For example, plane 501 consists of arrows, 508 and 509, to indicate to the user that 508 should point to the left of the level, and 509 should point to the posterior direction of the level. Such planes can be shown at multiple spinal levels, as shown in 502 to 505 for four additional levels. In FIG. 9A, the planes are positioned at the center of each spine level. Alternatively, it may be advantageous instead to position the plane at the end plate of each spinal level, which is easier to identify by the user compared to the center of a spinal level. This is shown in FIG. 9B, where planes 511 to 515 defining the orientation of five spinal levels are displayed.

Positioning of the planes may be assisted by also showing the planes in 2D views of the image data. As shown in 506, coronal slices of the image data showing planes 501 to 505 can be displayed to the user, enabling further fine tuning of the planes by interacting with the line representation of the planes in 2D. Sagittal slices 507 can also be presented to the user to give a different view to fine tune the orientation of the planes. A similar representation is shown in 516 and 517, showing the 2D representation of the planes 511 to 515. One or more methods (such as any of the preceding example methods) may be used in combination for defining a reference location of a spinal level. For example, the aforementioned region growing method may be employed as a first step, followed by receiving user input to further refine the position and orientation vector of each spinal level before use in determining the intraoperative level positions.

Figure 6A:
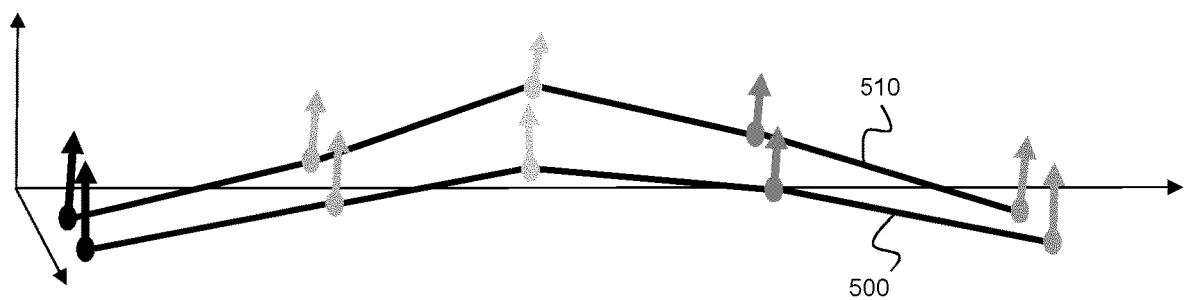
FIG. 6A shows an example of feedback presented on a user interface, where the example feedback is provided in the form of a center of mass and a posterior direction of the preoperative and intraoperative spinal orientations for each spinal level.

Once the intraoperative spine orientation has been obtained, the degree of residual kyphosis, lordosis or scoliosis can be assessed. In some example embodiments, one or more visualizations may be generated to display the intraoperative positions and/or orientations of the spinal levels, optionally compared to the preoperative volumetric positions and/or orientations of the corresponding spinal levels. For example, deformation of the spine may be visualized by a 3D plot, where a location and a vector may be used to depict the position of each spinal level relative to other levels, as shown in FIG. 6A comparing the spinal positions and orientations as determined from the volumetric frame of reference 500 to the spinal positions determined in the intraoperative frame of reference 510. For example, the position can be used to represent the center of the spinal level (or another suitable reference location), and the vector can represent the 'posterior' orientation of the spinal level. These point and vector pairs may be extracted as described above from the volumetric frame of reference 500, which can then be transformed by the corresponding per-level registration transform to generate the corresponding intraoperative positions and/or orientations 510.

Figure 6B:
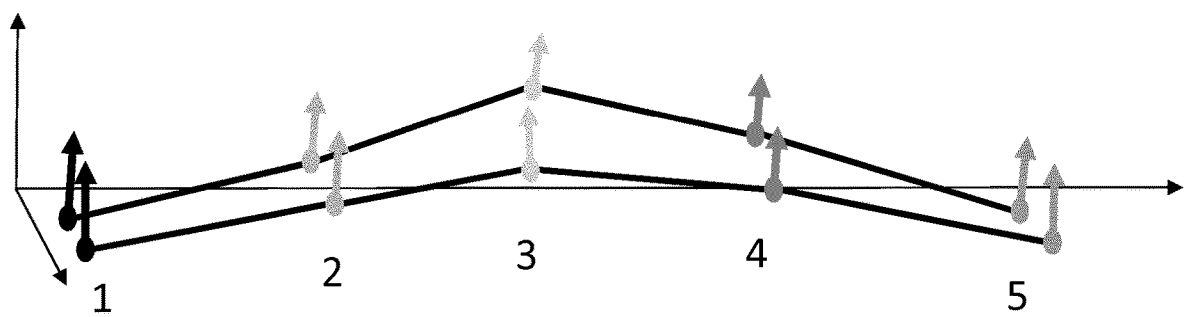
FIG. 6B shows an example of feedback presented on a user interface as shown in FIG. 6A, with the addition of numeric values denoting the change in distance of the center of mass and the angle of the posterior direction between the preoperative and intraoperative spinal orientations for each spinal level.
Figure 6C:
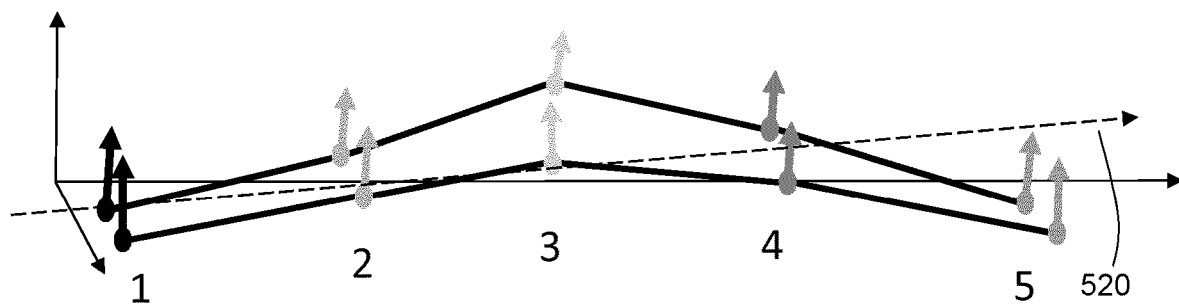
FIG. 6C shows an example of feedback presented on a user interface as shown in FIG. 6B, where the change in angle is relative to a user-defined axis.

In addition to the position and orientation, additional measures, such as, but not limited to, the difference in angle of the vector and displacement of the point can be displayed, as shown in FIG. 6B. In another example embodiment, evaluation of the change in spinal orientation may be assessed via user-guided techniques. For example, it may be advantageous for the user to define anatomical axes from which updated deformity measurements can be made. An example is shown in FIG. 6C, where an axis 520 is defined by the user. The generated report of the change in angles are made relative to this user-defined axis.

Figure 7A:
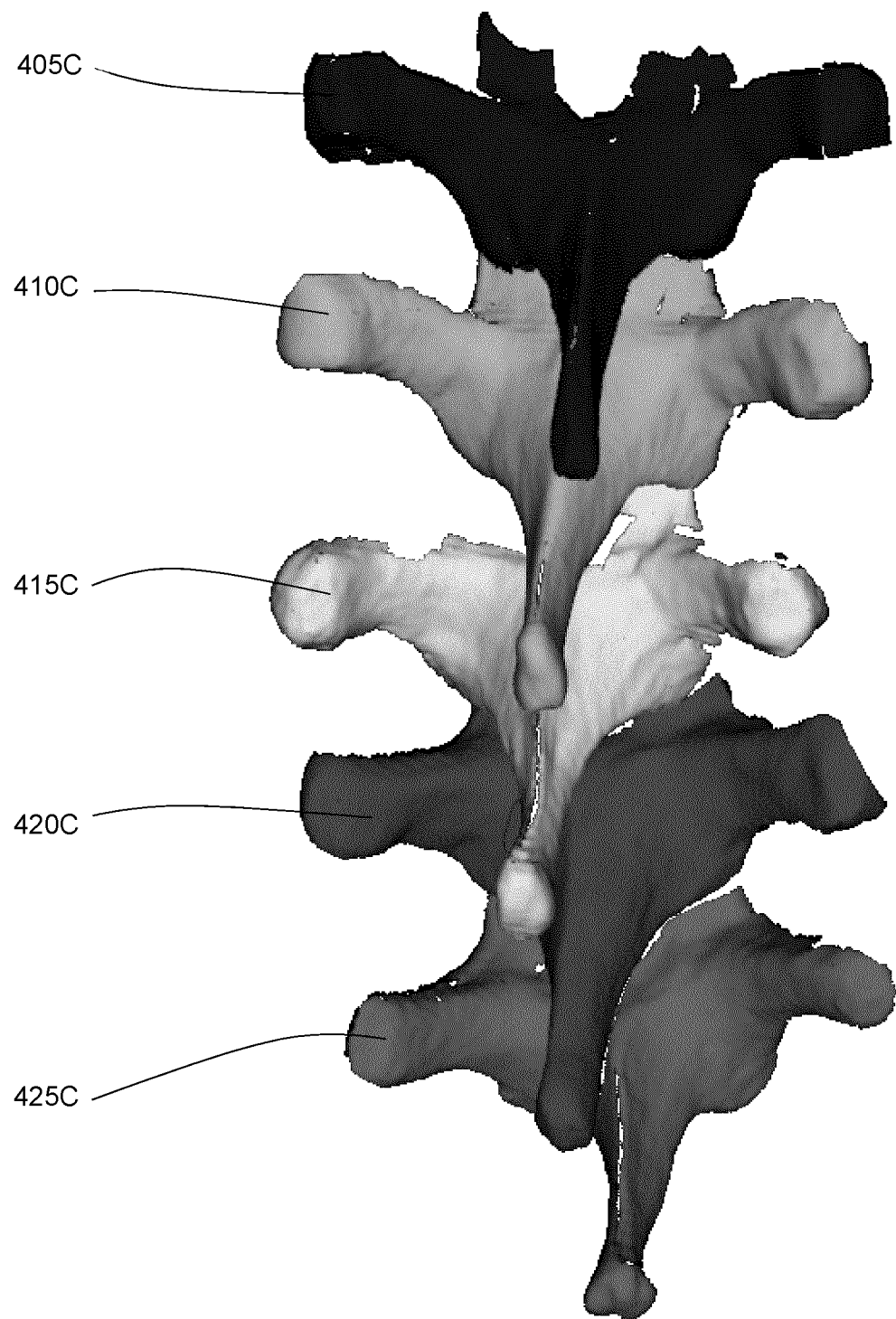
FIG. 7A shows an example of feedback presented on a user interface, where the intraoperative spinal orientation is displayed by updating the segmented surface data to match the intraoperative spinal orientation.

In an alternative embodiment, instead of visualizing a 3D plot, the intraoperative orientation of the spine may be visualized using the volumetric surface image generated from the volumetric image data, as shown in FIG. 7A, where the positions and orientations of the various levels are shown at 405C, 410C, 415C, 420C and 425C. Here, each segmented surface data associated with a corresponding spinal level is transformed by the corresponding per-level registration transform. This operation positions and orients each segmented surface data to represent the intraoperative orientation of the spine. This may be more intuitive, as it gives the user better context of each spinal level's position and orientation relative to adjacent spinal levels.

Figure 10:
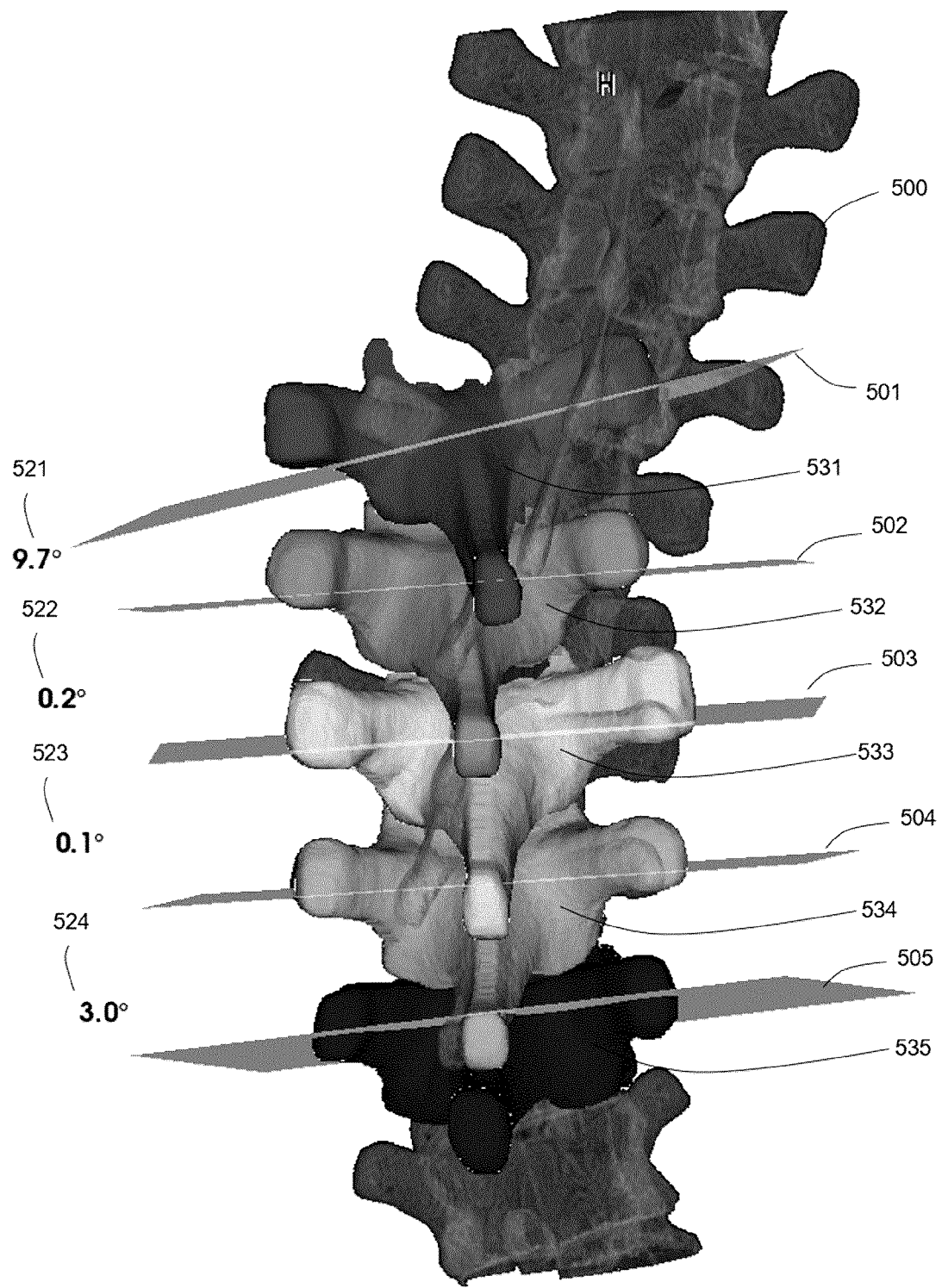
FIG. 10 shows an example of feedback presented on a user interface, wherein the preoperative and intraoperative position and orientation of spinal levels are displayed, with additional quantification information.
Figure 11:
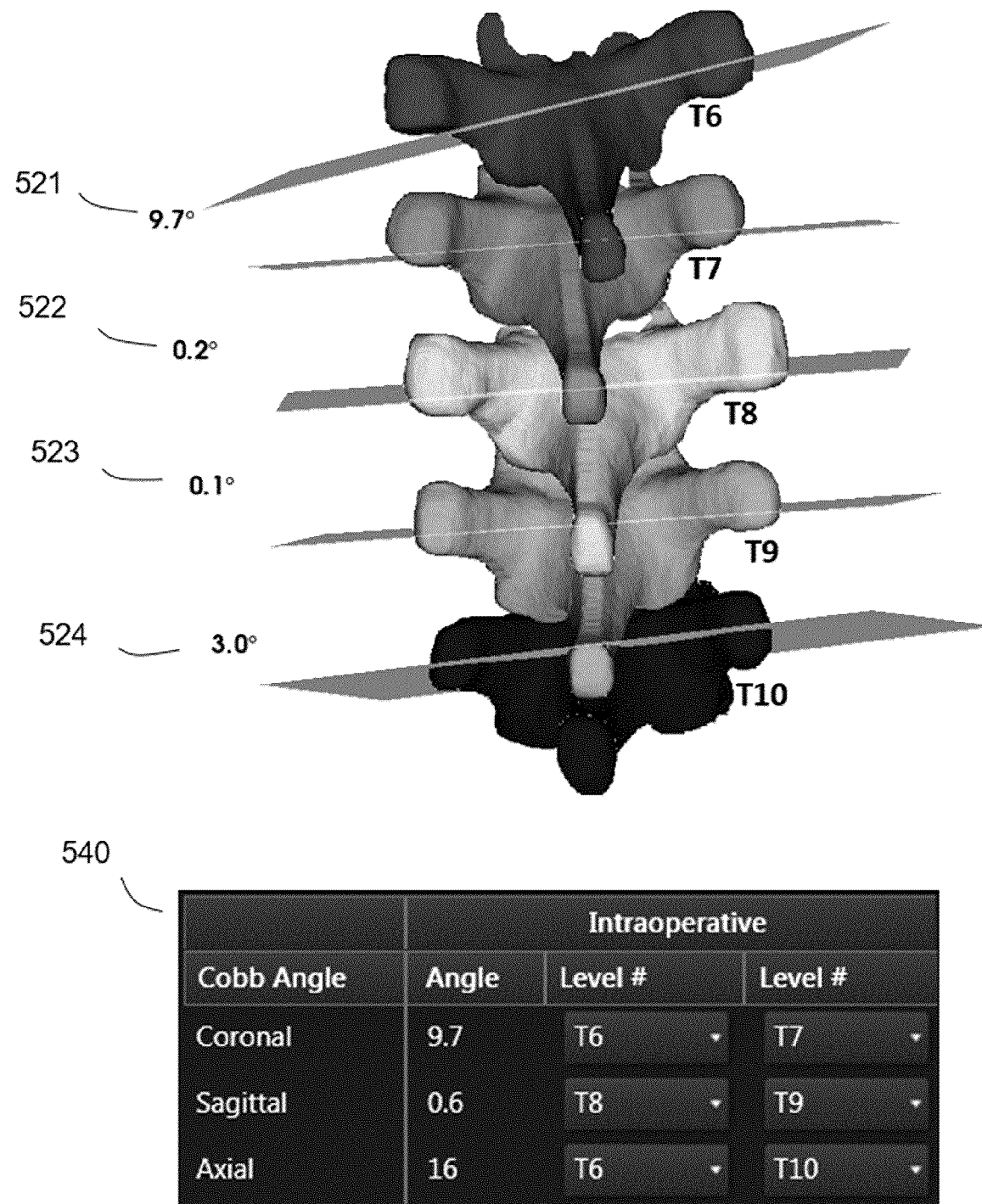
FIG. 11 shows an example of feedback presented on a user interface, in which the intraoperative angle between spinal levels is shown.

In some deformity surgeries, it may be advantageous to measure and display the angle between adjacent spinal levels intraoperatively to confirm that the correction of a deformity, such as scoliosis of the spine, has been achieved. Furthermore, it may be advantageous to visually observe the correction that has been attained during a procedure and compare that with a preoperative view of the spine. FIG. 10 shows an example of such a display, where the intraoperative orientation of five spinal levels 531 to 535 are shown, and is overlaid on top of the preoperative bone surface 500 of the spine. In this view, the lowest spinal level (towards the feet) 535 serves as an anchor point with the corresponding level in the preoperative bone surface of the spine. Alternatively, the intraoperative and preoperative orientation of the spine can be shown side by side, without overlay. Planes 501 to 505, as previously defined based on the preoperative spine orientation, are shown in this example, where the plane orientations have been updated to match the orientation of the corresponding intraoperative spinal levels. In some example implementations, angles can be calculated between these planes. For example, the angle between spinal levels 531 and 532, as defined by their corresponding vector of the planes projected in the coronal plane is shown in 521. Similar angles are displayed as 522, 523, and 524. Angles in other planes, such as the axial and sagittal planes, can be similar shown. In another example implementation, a graphical user interface 540 can be provided that enables the user to determine the angle between pairs of spinal levels in the coronal, sagittal, and axial plane by selecting from a menu, which can be used to measure Cobb angles. An example of such a graphical user interface is shown in FIG. 11.

Another example embodiment of assessing the intraoperative orientation of the spine may include the insertion of two or more user-defined measurement planes and/or vectors, associated with two or more levels. This can take the form of an adjustable overlay displayed on top of the volumetric data visualization. This enables measurement of relative angulation between two or more levels in user-defined planes. Additional metrics that may also be extracted include, but are not limited to sacral slope, pelvic incidence, pelvic tilt, sagittal vertical axis and coronal shift.

Some of the preceding example implementations employ the computed registration transforms to generate feedback pertaining to changes in the positions and orientations of the spinal levels from the time at which the volumetric image data was acquired to the time at which the intraoperative surface image data was obtained. As noted above, in some implementations, the volumetric image data may be obtained preoperatively. In other example implementations, the volumetric image data may be obtained intraoperatively, using an intraoperative volumetric imaging modality, such that the feedback showing the changes in positions and orientations of the spinal levels as they relate to intraoperative changes. In another example embodiment involving intraoperative changes, two or more intraoperative surface measurements may be obtained, at different times during a surgical procedure, and the aforementioned methods (using registration transforms relative to segmented surface data obtained based on volumetric image data) may be obtained to determine, for each associated surface measurement, the intraoperative positions and orientations of the exposed spinal levels. The different intraoperative positions and orientations of the spinal levels at these time points may be employed to generate feedback indicative of intraoperative changes between time points associated with the intraoperative surface measurements.

Figure 7B:
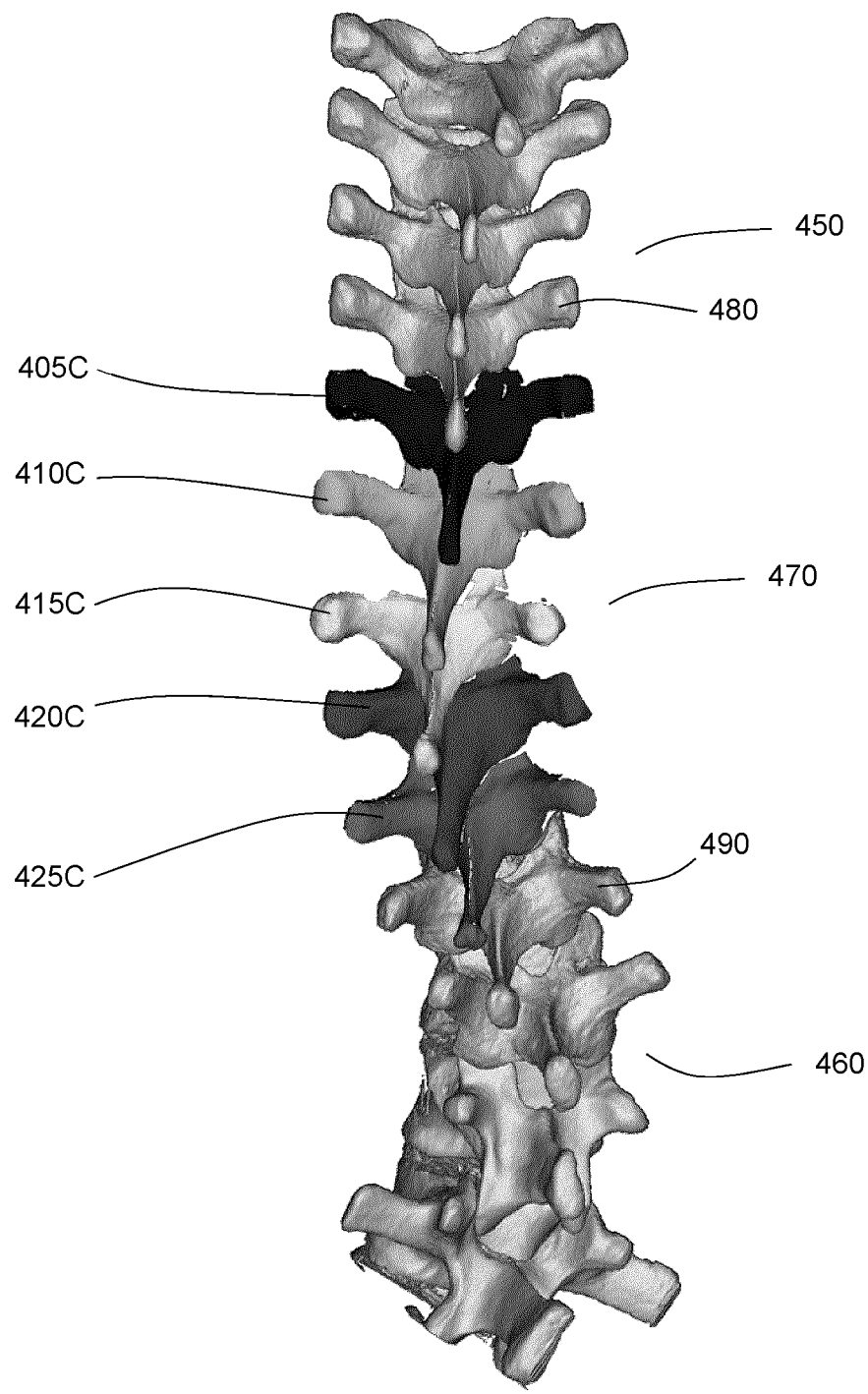
FIG. 7B shows an example of feedback presented on a user interface as shown in FIG. 7A, where additional spinal levels are shown by extrapolating the orientation of the spine beyond the intraoperatively exposed spinal levels.

It may be advantageous in some cases to show additional spinal levels present in the volumetric data that are not intraoperatively exposed. This is shown in FIG. 7B, where the additional set of spinal levels 450 and 460 are obtained from the multi-level surface data, and positioned and oriented above and below, respectively, the set of intraoperatively exposed spinal levels 470. To determine the position and orientation of the set of spinal levels 450 and 460 relative to the intraoperatively exposed region, additional volumetric fiducials are obtained in the adjacent spinal levels above (480) and below (490) the intraoperatively exposed region. Following the same method described earlier to process the multi-level surface data to generate segmented surface data, two additional inter-level transforms can be determined for these spinal levels adjacent to the intraoperatively exposed region. The set of spinal levels whose positions and orientations are to be extrapolated can be obtained by subtracting the segmented surface data 405C, 410C, 415C, 420C, and 425C from the multi-level surface data. The inter-level transforms can then be applied to the 450 and 460 accordingly to show their extrapolated position and orientations.

In the example embodiment described above and illustrated in the flow chart shown in FIG. 4A, per-level volumetric fiducial points and corresponding per-level intraoperative fiducial points are employed to register the segmented surface data, on a per-level basis, to the intraoperative surface data. In one example embodiment, the volumetric fiducial points are obtained based on input from a user or operator. For example, a user may employ a user interface to select, on a display showing the multi-level surface data, at least three volumetric fiducial points for each level. As noted above, surface segmentation of the multi-level surface data to obtain segmented surface data for a given level may be performed using at least one volumetric fiducial point from the given level to initialize a region growing surface segmentation method.

The per-level intraoperative fiducial points may also be obtained based on input from a user or operator. In one example implementation, a user may employ a tracked probe (e.g. a probe having fiducial markers attached thereto that are tracked with a tracking system) to select, via contact with different locations on the spine, intraoperative fiducial points for each level, where the intraoperative fiducial points correspond to the volumetric fiducial points on a per-level basis. In such a case, a tracked reference frame attached to the subject (e.g. reference frame 55 shown in FIG. 1) may be employed to compensate for the motion of the spine during point selection.

In one example embodiment, volumetric fiducial points are obtained for a pre-selected level, based on input from a user or operator, and the remaining volumetric fiducial points (and the segmented surface data) are automatically generated for the other spinal levels (e.g. the levels known or expected to be intraoperatively exposed). An example of such a method is illustrated in FIG. 4B.

Figure 4B:
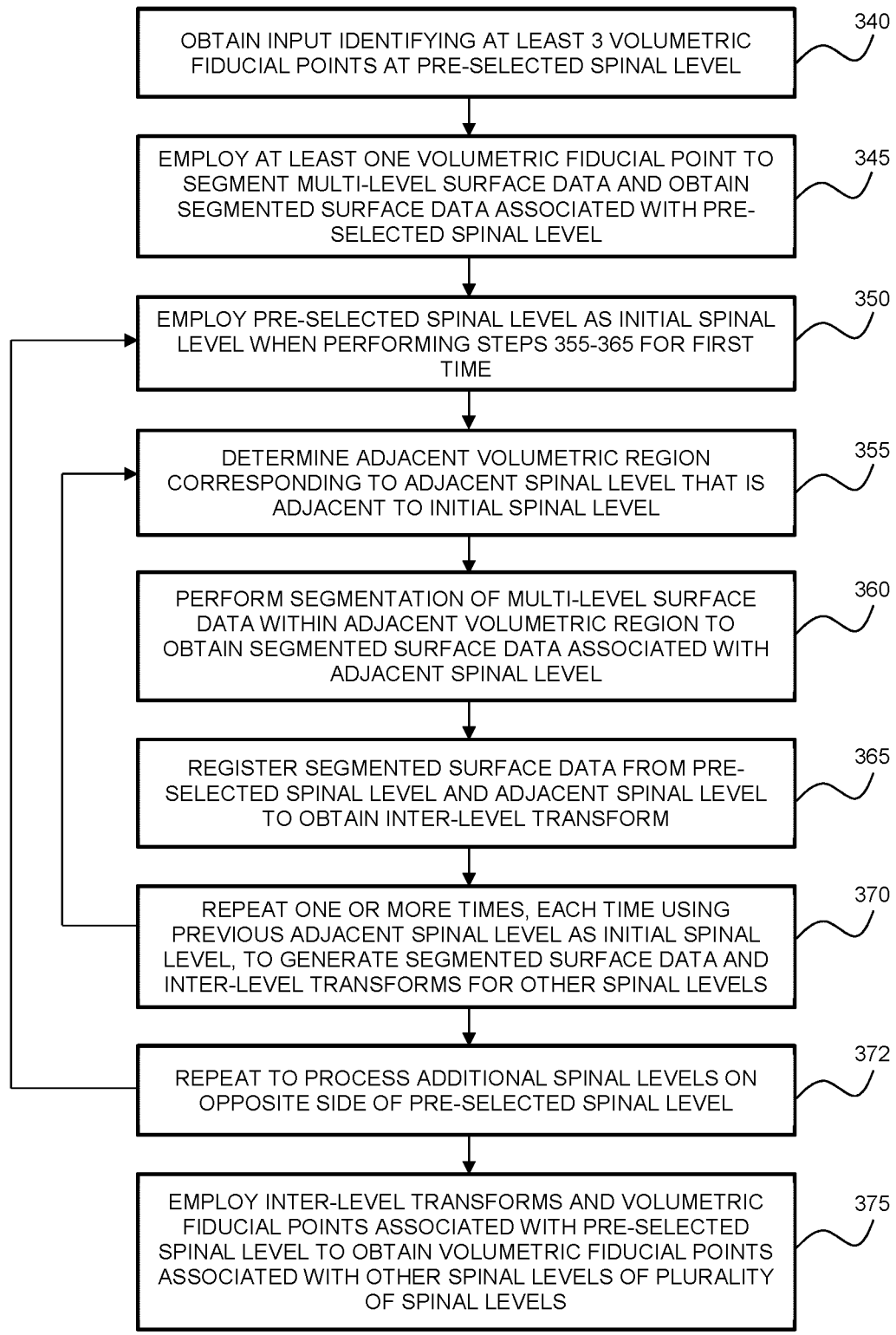
FIG. 4B is a flow chart illustrating an example method of generating segmented surface data and volumetric fiducial points for a set of spinal levels in the volumetric frame of reference, based on volumetric fiducial points identified at a pre-selected spinal level.

As shown at step 340 of FIG. 4B, input is received from a user identifying, in the multi-level surface data, at least three volumetric fiducial points associated with a pre-selected level that is expected to be exposed during the surgical procedure. For example, as shown in FIG. 2A, the multi-level surface 210 is employed for the selection of a set of at least three volumetric fiducial points, shown at 230A-C, at the pre-selected spinal level 220. The volumetric fiducial points 230A-C, which may be selected by an operator on a user interface displaying the multi-level surface data 210, identify the pre-selected spinal level 220 that is expected to be exposed during a surgical procedure.

Having identified the volumetric fiducial points 230A-C, the multi-level surface data 210 may be processed to generate the segmented surface data associated with the pre-selected level 220, as shown at step 345 in FIG. 4B. An example of the segmented surface data 250 is shown in FIG. 2B, which also shows the volumetric fiducial points 230. The segmented surface data 250 includes surface data corresponding to the pre-selected level 220. Segmentation of the multi-level surface data to obtain the segmented surface data may be performed according to any suitable method. One or more of the volumetric fiducial points may be employed to initiate surface segmentation.

Having performed surface segmentation of the pre-selected spinal level, the pre-selected spinal level, and its associated segmented surface data, is employed for the generation of segmented surface data associated with an adjacent spinal level, as shown in steps 350 to 365 of FIG. 4B. An example of an adjacent level is shown in FIG. 2A at 220B. Unlike the pre-selected spinal level 220, the adjacent spinal level 220B does not have associated volumetric fiducial points to support surface segmentation from the multi-level surface data, or to support registration with the intraoperative surface data.

In order to facilitate surface segmentation of an adjacent spinal level, an adjacent volumetric region, such as a bounding box (the region need not be a rectangular prism) is identified in which to perform segmentation, as shown at step 355. The determination of the adjacent volumetric region may be made based on a determination of directional information associated with the orientation of the spine, where the directional information enables the determination of a direction in which to locate the adjacent spinal level. The directional information can be a direction which defines the entire spine. Alternatively, the directional information can be described by a spline or a piece-wise linear function to follow the shape of the spine.

This directional information may be obtained according to a variety of methods, non-limiting examples of which are provided below. In one example implementation, the directional information may be obtained from information associated with the volumetric image data, such a superior-inferior direction provided from the DICOM header. In another example implementation, an axis associated with the orientation of the spine may be determined from principal component analysis. In another example implementation, image processing methods may be applied to the volumetric image data to extract an estimated shape of the spine.

In one example implementation, a set of local spine axes may be determined, thereby providing directional information on a per-level basis. A preferential axis is initially determined for segmenting the volumetric image data. The preferential axis may be determined, for example, from information associated with the volumetric image data, such a superior-inferior direction provided from a DICOM header, or from principle component analysis. The preferential axis may then be employed to segment the volumetric image data into a series of volumetric slabs that are arranged along the preferential axis, each of which are analyzed to locate the spine. The choice of slab thickness depends on the resolution required for computing the directional information of the spine. On the other hand, if the slab thickness is too thin, the accuracy of the finding the spine within the slab, and hence deriving the directional information, may be degraded, due to reduction of signal (e.g. structured belong to the spine) to noise (e.g. the background). A slab thickness of approximately half of the length of a spinal level is typically suitable.

Various methods can be employed to analyze the slabs in order to derive the directional information of the spine. One example method can be template-based, wherein the slabs are compared to a pre-computed atlas of different vertebra. Alternatively, a user-defined threshold can be used to define a contour and/or isosurface of the bone, from which the vertebra region within the slab can be identified. The vertebra region can be identified by performing an iterative search for structures that resemble the vertebra according to a pre-computed atlas. Alternatively, an atlas-free method can be employed, which utilizes one or more volumetric fiducial points as a starting point via an iterative search.

For the atlas-free method, an initial volumetric slab segment containing one or more of the volumetric fiducial points is identified. An initial bounding box (or other suitable confining volumetric region) is then determined, where the initial bounding box contains, and is centered on, or approximately centered on, one or more of the fiducial points. The size of the initial bounding box may be determined, for example, based on the spatial extent of the segmented surface data associated with the pre-selected spinal level, or based on an estimated spatial extent of an average spinal level. This initial volumetric slab segment is processed, within the initial bounding box, to determine an initial center of mass of bony structures within the initial volumetric slab segment. This process may be repeated one or more times, where each time, the bounding box is re-centered on the most recently identified center of mass location. The center of mass location may be iteratively refined in this manner until a pre-selected convergence criterion has been met, such as the change in the center of mass location between subsequent iterations is below a threshold.

Once the center of mass corresponding to the spine has been determined in the initial volumetric slab, an adjacent bounding box may then be determined, within an adjacent slab. Since the bounds of a vertebra is approximately the same within the same patient, the adjacent bounding box can be of the same size as the bounding box from the initial volumetric slab, wherein the center of the adjacent bounding box can be initialized with the center of mass from the initial volumetric slab. This adjacent volumetric slab segment is processed similarly, within the adjacent bounding box, to determine an adjacent center of mass location within the adjacent volumetric slab segment. As noted above, this process may be repeated one or more times, where each time, the bounding box is re-centered on the most recently identified center of mass location, iteratively refining the center of mass location until a pre-selected convergence criterion has been met.

The above method of finding an adjacent center of mass location in an adjacent volumetric slab segment may then be repeated one or more times in order to determine center of mass locations within a plurality of the volumetric slab segments, thereby allowing the determination of a local axis, based on two or more center of mass locations. In one example implementation, the local axis associated with two neighboring volumetric slab segments may be employed to locate the bounding box within an adjacent volumetric slab region when performing the aforementioned method.

In situations where the initial preferential axis is significantly different than the directional information of the spine (e.g. due to disease), the computed directional information can be used to again segment the volumetric image data into a series of volumetric slabs, and the above iterative center finding method repeated to refine the directional information of the spine.

After obtaining the directional information (e.g. global or local), this information may be employed to determine an adjacent volumetric region within which to perform segmentation of the multi-level surface data in order to obtain the adjacent segmented surface data corresponding to the adjacent spinal level, as per step 355 of FIG. 4B. For example, an adjacent bounding box for segmenting the adjacent spinal level may be centered at a location, relative to one or more of the volumetric fiducial points, which lies along an axis obtained based on the directional information, such that the bounding box is expected to contain the adjacent spinal level. The spatial separation between the center of the adjacent bounding box and the one or more volumetric fiducial points may be determined, for example, based on the spatial extent of the segmented surface data associated with the pre-selected spinal level, or based on reference anatomical data (e.g. atlas data) characterizing an estimated spatial separation between the pre-selected spinal level and the adjacent spinal level.

The multi-level surface data may then be processed within the adjacent bounding box to generate the segmented surface data associated with the adjacent spinal level, as shown at step 360. As noted above, the segmentation of the multi-level surface data to obtain the adjacent segmented surface data may be performed according to any suitable method.

An inter-level transform is then determined between the pre-selected spinal level and the adjacent spinal level, as shown at step 365. The inter-level transform between the pre-selected spinal level and the adjacent spinal level may be determined by performing registration between the segmented surface data (associated with the pre-selected spinal level) and the adjacent segmented surface data (associated with the adjacent spinal level). The inter-level transform between the segmented surface data of the pre-selected spinal level and the adjacent segmented surface data is defined by following the pre-computed directional information, translating by a distance that is based on the spatial extent of the segmented surface data, or using reference anatomical data (e.g. atlas data) characterizing an estimated spatial separation between the initial spinal level and the adjacent spinal level. Fine-tuning of the registration is then performed by any suitable registration algorithm. It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

Having obtained the inter-level transform between segmented surface data of the pre-selected spinal level and the adjacent segmented surface data, the position and orientation of the adjacent spinal level, relative to that of the pre-selected spinal level, is known. This process of determining the segmented surface data for an adjacent spinal level, and an inter-level transform from the initial spinal level to the adjacent spinal level, may then be repeated for additional adjacent spinal levels, as shown at step 370. As per step 350, when steps 355-365 are performed for the first time, the pre-selected spinal level is employed as an initial level for determining the segmented surface data and the inter-level transform to the adjacent spinal level. However, as per step 370, each time steps 355-365 are repeated, the previous adjacent level is employed as the initial level, such that the newly determined segmented surface data and the newly determined inter-level transform pertains to the next adjacent spinal level. This process is repeated if other spinal levels, of the plurality of spinal levels that are intraoperative exposed, reside on the opposing side of the pre-selected spinal level.

After having performed steps 340 to 372, segmented surface data is obtained for each spinal level, and inter-level transforms are obtained between each set of adjacent spinal levels, based on the volumetric fiducial points provided for the pre-selected spinal level. As shown at step 375, the inter-level transforms may be applied to volumetric fiducial points in order to generate, on a per-level basis, volumetric fiducial points associated with the additional spinal levels.

Figure 3A:
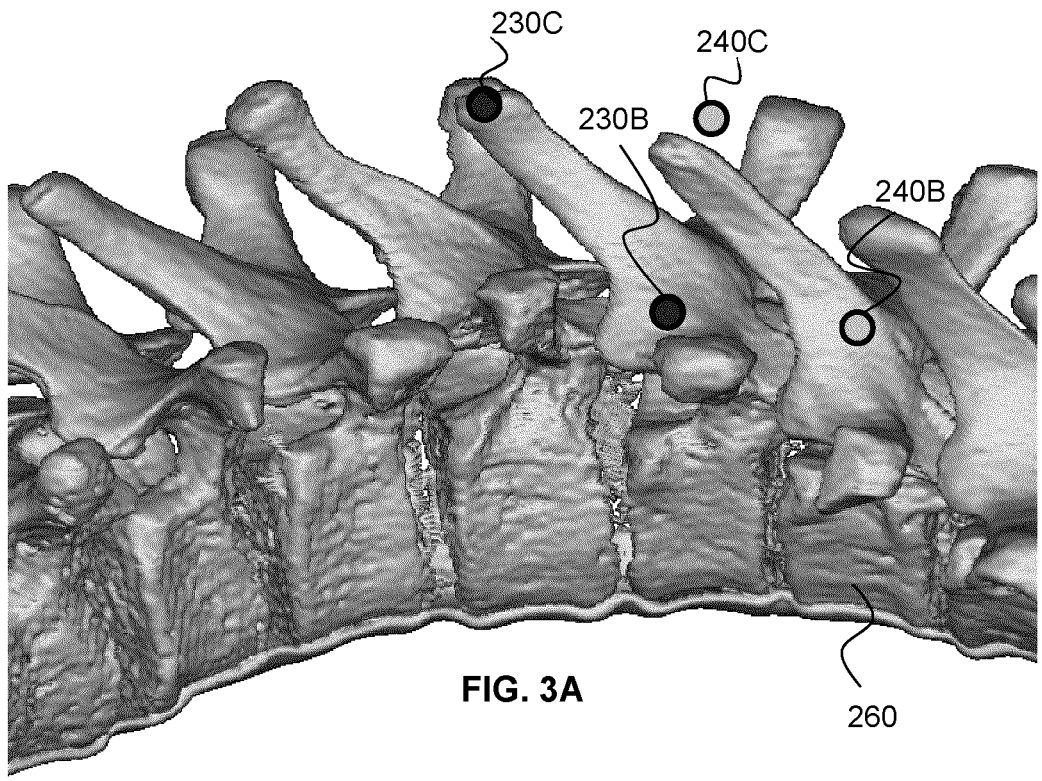
FIG. 3A illustrates the process of shifting the volumetric fiducial points via the inter-level transform, in order to generate adjacent volumetric fiducial points at an adjacent spinal location.

As a first step, the inter-level transform between the pre-selected spinal level and the adjacent spinal level may be employed to determine locations, in the adjacent segmented surface data, of adjacent volumetric fiducial points. According to this example implementation, and as illustrated in FIG. 3A, the inter-level transform may be applied to the locations of the volumetric fiducial points 230A-C associated with the pre-selected fiducial points in the volumetric frame of reference, such that the volumetric fiducial points 230A-C are transformed to the region associated with the adjacent spinal level (FIG. 3A shows volumetric fiducial points 230B and 230C, as volumetric fiducial point 230A is hidden in the view shown).

Figure 3B:
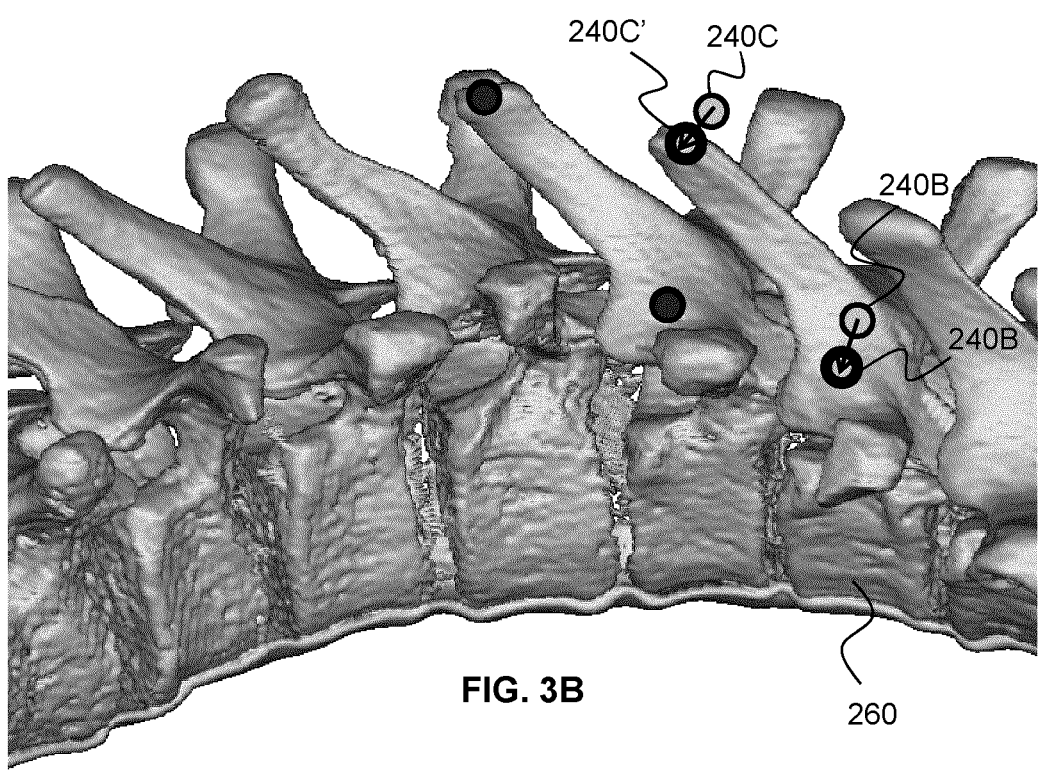
FIG. 3B demonstrates an example method of "snapping" the shifted volumetric fiducial points onto the adjacent segmented surface.

Since the segmented surface data that is associated with the pre-selected spinal level is different than the adjacent segmented surface data associated with the adjacent level, the transformed volumetric fiducial points 240A-C may not lie within the adjacent surface data. This effect is illustrated in FIG. 3B, where, for example, transformed points 240B and 240C initially lie above the adjacent segmented surface 260. In order to bring the transformed points 240A-C into the adjacent segmented surface data, the transformed points 240A-C may be shifted so that they lie within the adjacent segmented surface, as shown at points 240B' and 240C' in FIG. 3B.

For example, this may be achieved by computing a location within the adjacent segmented surface data that is nearest to the transformed point, and shifting ("snapping") the transformed point to this nearest location, thereby obtaining the adjacent volumetric fiducial point that lies within the adjacent segmented surface data. Alternatively, the point shifting procedure may be performed by computing the local surface normal vector that is directed at the transformed fiducial point, and shifting the transformed fiducial point along the direction corresponding to this vector. Optionally, in combination with these methods of shifting the fiducials, multiple candidate nearest locations on the adjacent segmented surface may be evaluated, wherein the choice is made on a similarity measure of each candidate to the fiducial on the segmented data. This similarity measure can be based on surface normals and curvatures in addition to proximity.

Figure 5A:
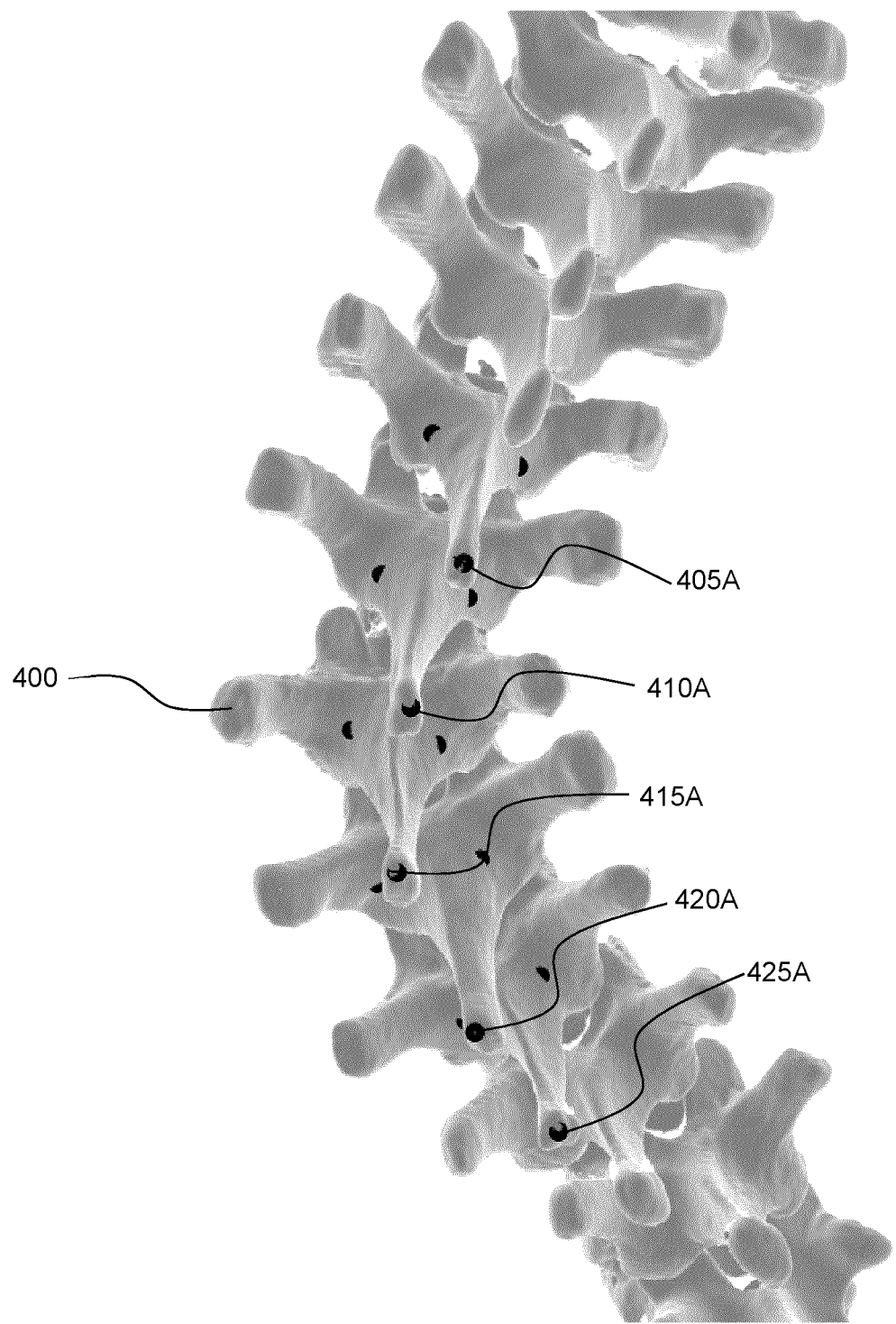
FIG. 5A illustrates the use of inter-level transforms among adjacent levels in order to generate, based on a set of selected volumetric fiducial points associated with a selected level, additional volumetric fiducial points associated with additional levels.
Figure 5B:
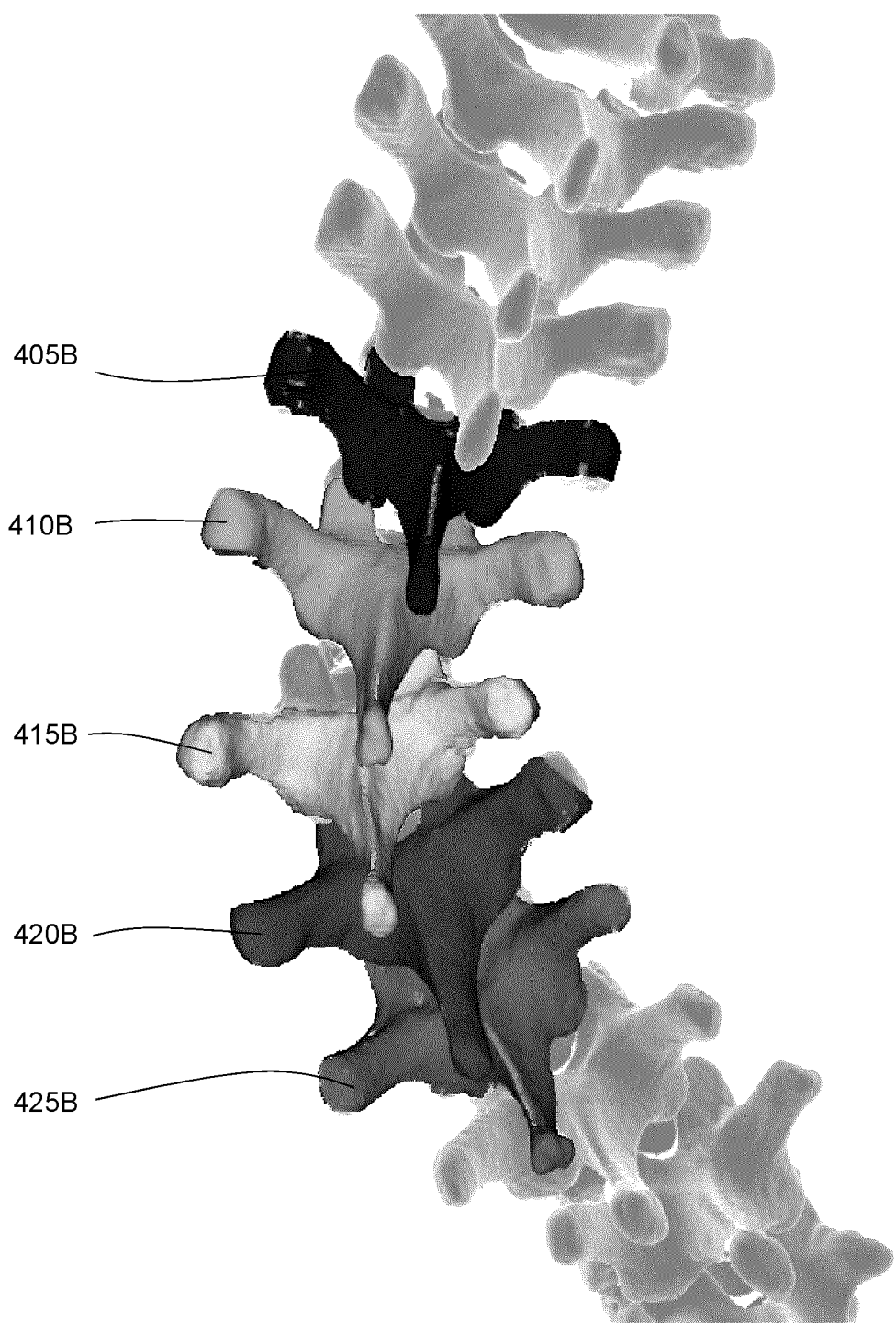
FIG. 5B illustrates a multi-level surface generated based on volumetric image data, showing the segmentation of surfaces associated with different levels to obtain per-level segmented surface data.

This process of generating adjacent volumetric fiducial points may be repeated to generate the volumetric fiducial points for the next adjacent spinal level, where the next inter-level transform is applied to the most recently determined adjacent volumetric fiducial points (e.g. after performing the aforementioned "snapping" process). This method may be repeated to generate the volumetric fiducial points for all of the relevant spinal levels, thereby generating a set of per-level volumetric fiducial points. This process is illustrated in FIGS. 5A and 5B, where user-identified volumetric fiducial point 415A associated with a pre-selected spinal level 400 is employed to generate per-level volumetric fiducial points 405A, 410A, 420A and 425A (shown in FIG. 5A) and per-level segmented surfaces 405B, 410B, 415B, 420B and 425B (shown in FIG. 5B).

As noted above, in one example embodiment, the intraoperative fiducial points may be provided manually via input from a user or operator. However, in another example embodiment, the intraoperative fiducial points may be obtained for a selected level, based on input from a user or operator, and where the intraoperative fiducial points for the selected level correspond to the volumetric fiducial points defined at a corresponding level in the volumetric reference frame. The intraoperative fiducial points are then automatically generated for the other spinal levels in the intraoperative reference frame. An example of such a method is illustrated in FIG. 4C.

Figure 4C:
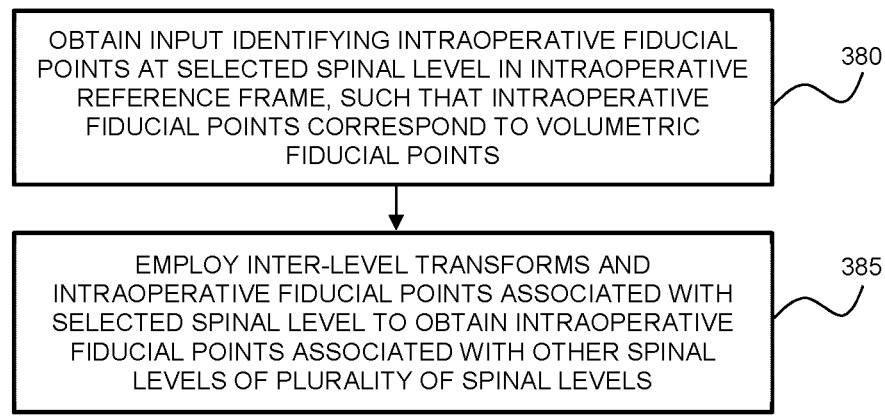
FIG. 4C is a flow chart illustrating an example method of generating intraoperative fiducial points for a set of spinal levels in the intraoperative frame of reference, based on intraoperative fiducial points identified at a selected spinal level.

As shown at step 380 of FIG. 4C, input is received from a user identifying, volumetric fiducial points associated with a selected level in the intraoperative frame of reference. In one example implementation, a user may employ a tracked probe (e.g. a probe having fiducial markers attached thereto that are tracked with a tracking system) to select, via contact with the spine at a selected level, the intraoperative fiducial points for the selected level, where the intraoperative fiducial points correspond to the volumetric fiducial points at a corresponding level in the volumetric frame of reference.

As per step 385, the inter-level transforms, defined among pairs of adjacent spinal levels in the volumetric reference frame (as explained above) may then be employed to generate the intraoperative fiducial points for the other spinal levels in the intraoperative frame of reference. If the volumetric fiducial points for the spinal levels were generated automatically, then these inter-level transforms will have already been computed. If the volumetric fiducial points were defined manually, then the inter-level transforms in the volumetric frame of reference may be determined by generating segmented surface data for each spinal level, using at least one of the volumetric fiducial points for each level to initiate segmentation, and then performing surface registration among adjacent levels, as per the method described above.

As a first step when generating adjacent intraoperative fiducial points, the inter-level transform between the spinal level in the volumetric frame of reference that corresponds to the selected spinal level in the intraoperative frame of reference, and the adjacent spinal level, may be employed to determine locations in the intraoperative reference frame, of adjacent intraoperative fiducial points. This method operates under the assumption that even through the spine orientation will likely have changed in the intraoperative frame of reference relative to the spine orientation in the volumetric frame of reference, the inter-level change between adjacent levels will be sufficiently small such that the inter-level transform from the volumetric frame of reference is a valid approximation of the spatial relationship between adjacent levels in the intraoperative frame of reference.

According to this example implementation, the inter-level transform (obtained from the volumetric frame of reference) may be applied to the locations of the intraoperative fiducial points associated with the region associated with the pre-selected spinal level in the intraoperative frame of reference, such that the intraoperative fiducial points are transformed to the region associated with the adjacent spinal level, in a manner similar to the illustration in FIG. 3A. Registration may then be performed between the adjacent segmented surface data and the intraoperative surface data, where the adjacent volumetric fiducial points and adjacent intraoperative fiducial points are used to perform an initial registration, followed by a surface-to-surface registration, as shown at steps 320 and 325 in FIG. 4A, to obtain the per-level registration transform.

It is noted that the aforementioned method of generating adjacent intraoperative fiducial points is an approximation, and extending these fiducial points beyond the adjacent spinal level can lead to accumulation of errors. Accordingly, in one example implementation, the intraoperative fiducial points may be refined by using the per-level registration transform previously computed between the adjacent segmented surface data and the intraoperative surface data. In this example method, the intraoperative fiducials associated with the region associated with the pre-selected spinal level in the intraoperative frame of reference are first transformed into the volumetric frame of reference, using the per-level registration transform corresponding to the pre-selected spinal level. The inter-level transform is then used to further transform the position of these intraoperative fiducial points into the adjacent spinal level, in the volumetric frame of reference. As a further refinement, the transformed fiducial points are shifted so that they lie within the adjacent segmented surface data as previously described, analogous to the illustration in FIG. 3B. Finally, the fiducials points are transformed back into the intraoperative frame of reference using the per-level registration transform corresponding to the adjacent spinal level.

This method may be repeated to generate the intraoperative fiducial points for all of the relevant spinal levels, thereby generating a set of per-level intraoperative fiducial points, where errors introduced by the use of the inter-level transforms are iteratively corrected both by using the inter-level registration transforms and snapping the points into the intraoperative surface, as described above.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of determining an intraoperative orientation of a spine, the method comprising:
obtaining volumetric image data pertaining to a spine;
processing the volumetric image data to generate multi-level surface data characterizing a bone surface of the spine;
processing the multi-level surface data to generate segmented surface data on a per-level basis for each level of a plurality of spinal levels;
intraoperatively detecting, with a surface detection subsystem, intraoperative surface data characterizing surface regions associated with each spinal level of the plurality of spinal levels;
for each spinal level of the plurality of spinal levels:
employing volumetric fiducial points associated with said each spinal level and corresponding intraoperative fiducial points associated with said each spinal level to perform an initial registration between the segmented surface data associated with said each spinal level and the intraoperative surface data, and subsequently performing a surface-to-surface registration between the segmented surface data associated with said each spinal level and the intraoperative surface data, thereby obtaining a registration transform associated with said each spinal level; and
employing the registration transforms associated with the plurality of spinal levels to generate measures associated with an intraoperative spinal orientation, and providing feedback based on the measures.

2. The method according to claim 1 wherein the feedback includes a visualization of intraoperative positions and orientations of the spinal levels.

3. The method according to claim 2 wherein the visualization associates, with each spinal level of the plurality of spinal levels, a location of the level and a vector indicative of the orientation of the level, wherein the location and the vector are determined based on the registration transforms.

4. The method according to claim 2 wherein the visualization comprises a three-dimensional image of the spine generated based on the registration transforms.

5. The method according to claim 1 wherein the feedback includes one or more parameters quantifying the intraoperative orientation and/or position of the spinal levels.

6. The method according to claim 5 wherein the one or more of the parameters comprise angles characterizing the intraoperative orientations of the spinal levels.

7. The method according to claim 6 wherein one or more of the parameters comprise angles of the spinal levels.

8. The method according to claim 6 wherein one or more of the parameters comprise differences in angles of adjacent spinal levels.

9. The method according to claim 5 wherein the one or more parameters comprise distances characterizing relative intraoperative positions of the spinal levels.

10. The method according to claim 5 wherein one or more of the parameters are selected from the group consisting of sacral slope, pelvic incidence, pelvic tilt, sagittal vertical axis and coronal shift.

11. The method according to claim 1 wherein the feedback includes a visualization showing changes in the intraoperative orientations and positions of the spinal levels relative to the orientations and positions of the spinal levels associated with the volumetric image data.

12. The method according to claim 1 wherein the feedback includes one or more parameters quantifying changes in the intraoperative orientations and/or positions of the spinal levels relative to respective orientations and/or positions of the spinal levels associated with the volumetric image data.

13. The method according to claim 12 wherein the one or more parameters include angles characterizing changes in intraoperative orientations of the spinal levels relative to the orientations of the spinal levels associated with the volumetric image data.

14. The method according to claim 12 wherein the one or more parameters include distances characterizing changes in intraoperative positions of the spinal levels relative to positions of the spinal levels associated with the volumetric image data.

15. The method according to claim 1 wherein the volumetric fiducial points are defined, for each spinal level, according to input from an operator.

16. The method according to claim 1 wherein the intraoperative fiducial points are defined, for each spinal level, according to input received from an operator.

17. The method according to claim 16 further comprising:
employing a tracking system to track the position and/or orientation of a fiducial marker intraoperatively attached to the spine while obtaining the input identifying the intraoperative fiducial points associated with each spinal level to compensate for the motion of the spine.

18. The method according to claim 1 wherein the segmented surface data and the volumetric fiducial points associated with each spinal level of the plurality of spinal levels are obtained by:
(i) obtaining input identifying at least three volumetric fiducial points at a pre-selected spinal level within a volumetric frame of reference associated with the volumetric image data;
(ii) employing at least one of the volumetric fiducial points associated with the pre-selected spinal level to perform segmentation on the multi-level surface data, thereby obtaining segmented surface data associated with the pre-selected spinal level;
(iii) employing the pre-selected spinal level as an initial spinal level when performing steps (iv) to (vi) for a first time;
(iv) determining an adjacent volumetric region, within the volumetric frame of reference, that is associated with an adjacent spinal level that is adjacent to the initial spinal level;
(v) performing segmentation on the multi-level surface data within the adjacent volumetric region, thereby obtaining adjacent segmented surface data associated with the adjacent spinal level;
(vi) registering the segmented surface data associated with the initial spinal level to the adjacent segmented surface data, thereby obtaining an inter-level transform between the initial spinal level and the adjacent spinal level;
(vii) repeating steps (iv) to (vi) one or more times, each time using the previous adjacent level as the initial level, to generate segmented surface data and the inter-level transforms associated with additional spinal levels of the plurality of spinal levels on a first side of said pre-selected spinal level, such that each inter-level transform is between adjacent spinal levels;
(viii) repeating steps (iii) to (vii) if additional spinal levels of said plurality of spinal levels reside on the other side of said pre-selected spinal level; and
(ix) employing the inter-level transforms and the volumetric fiducial points associated with the pre-selected spinal level to obtain volumetric fiducial points associated with the other spinal levels of the plurality of spinal levels.

19. The method according to claim 18 wherein employing the inter-level transforms and the volumetric fiducial points associated with the pre-selected spinal level to obtain volumetric fiducial points associated with the other spinal levels of the plurality of spinal levels comprises:
(x) applying the inter-level transform between the pre-selected spinal level and an adjacent spinal level to the volumetric fiducial points associated with the pre-selected spinal level, thereby obtaining estimated volumetric fiducial locations associated with the adjacent spinal level;
(xi) employing the estimated volumetric fiducial locations to determine volumetric fiducial points residing within the segmented surface defined by the segmented surface data corresponding to the adjacent spinal level; and
(xii) repeating steps (x) and (xi) to determine the volumetric fiducial points associated with the additional spinal levels of the plurality of spinal levels.

20. The method according to claim 18 wherein the intraoperative fiducial points are defined, for each spinal level, according to input received from an operator.

21. The method according to claim 18 wherein the intraoperative fiducial points are generated by:
obtaining input identifying at least three intraoperative fiducial points at a selected spinal level within an intraoperative frame of reference, wherein the selected spinal level in the intraoperative frame of reference is expected to correspond to the pre-selected spinal level in the volumetric frame of reference, and wherein the intraoperative fiducial points at the pre-selected spinal level correspond to the volumetric fiducial points at the pre-selected spinal level; and employing the inter-level transforms and the intraoperative fiducial points associated with the selected spinal level to obtain intraoperative fiducial points associated with the other spinal levels of the plurality of spinal levels.

22. The method according to claim 21 wherein employing the inter-level transforms and the intraoperative fiducial points associated with the selected spinal level to obtain intraoperative fiducial points associated with the other spinal levels of the plurality of spinal levels comprises:
(x) employing the registration transform between the pre-selected spinal level and the selected spinal level to transform the intraoperative fiducial points associated with the selected spinal level into the volumetric frame of reference, thereby obtaining transformed intraoperative fiducial points;
(xi) applying the inter-level transform between the pre-selected spinal level and the adjacent spinal level to the transformed intraoperative fiducial points, thereby obtaining estimated adjacent fiducial locations associated with the adjacent spinal level;
(xi) employing the estimated adjacent fiducial locations to determine transformed adjacent fiducial points residing within the segmented surface data associated with the adjacent spinal level;
(xii) employing the registration transform associated with the adjacent spinal level to transform the transformed adjacent fiducial points into the intraoperative frame of reference, thereby obtaining intraoperative fiducial points associated with the adjacent spinal level; and
(xiii) repeating steps (x) and (xii) to determine the intraoperative fiducial points associated with the additional spinal levels of the plurality of spinal levels.

23. The method according to claim 18 wherein the segmented surface data and the inter-level transforms are determined for spinal levels residing on both sides of the pre-selected spinal level.

24. The method according to claim 18 wherein the adjacent volumetric region is determined, at least in part, based on directional information associated with the orientation of the spine in the volumetric frame of reference.

25. The method according to claim 24 wherein when performing step (iv), the adjacent volumetric region is determined by:
determining a bounding box associated with the segmented surface data of the initial spinal level;
employing the directional information to translate the bounding box to a spatial region expected to contain the adjacent spinal level.

26. The method according to claim 24 wherein the directional information is determined employing one of: a DICOM header, principal component analysis, and spinal cord location extraction via image processing.

27. The method according to claim 24 wherein the directional information is determined by:
a) determining a preferential axis for processing the volumetric image data;
b) segmenting the volumetric image data into a series of volumetric slab segments arranged along the preferential axis;
c) identifying a volumetric slab segment containing at least one of the volumetric fiducial points;
d) determining an initial volumetric test region bounding the at least one of the volumetric fiducial points within the volumetric slab segment;
e) determining a center of mass location within the initial volumetric test region;
f) determining, based on the center of mass location, an adjacent volumetric test region within an adjacent volumetric slab segment, and determining an adjacent center of mass location within the adjacent volumetric test region;
g) repeating step f) one or more times to obtain a set of center of mass locations corresponding to different volumetric slab segments; and
h) processing the set of center of mass locations to determine the directional information characterizing the orientation of the spine.

28. The method according to claim 27 wherein when repeating step f) to identify an additional adjacent center of mass location within an additional adjacent volumetric slab segment, an additional adjacent volumetric test region within the additional adjacent volumetric slab segment is determined by translating a previously determined adjacent volumetric test region along a local axis, wherein the local axis is determined based on two center of mass locations corresponding to volumetric slab segments neighbouring the additional adjacent volumetric slab segment.

29. The method according to claim 27 wherein, when performing steps e) or f), the center of mass location that is determined is an estimated center of mass location, the method further comprising:
generating a refined center of mass by determining a second volumetric test region bounding the estimated center of mass location; and
determining the refined center of mass location within the second volumetric test region.

30. The method according to claim 29 further comprising repeating the determination of the refined center of mass one or more times until a pre-selected convergence criterion has been satisfied.

31. The method according to claim 1 wherein the segmented surface data associated with one or more of the spinal levels is obtained by performing region growing on the multi-level surface data.

32. The method according to claim 1 wherein the surface detection subsystem is a structured light subsystem.

33. The method according to claim 1 wherein the intraoperative surface data is acquired two or more times during a surgical procedure, and wherein a set of registration transforms are respectively calculated, and respective feedback is intraoperatively generated, each time that the intraoperative surface data is acquired.

34. A system for determining an intraoperative orientation of a spine, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to a spine to generate multi-level surface data characterizing a bone surface of the spine;
processing the multi-level surface data to generate segmented surface data on a per-level basis for each level of a plurality of spinal levels;
controlling said surface detection subsystem to intraoperatively detect intraoperative surface data characterizing surface regions associated with each spinal level of the plurality of spinal levels;

for each spinal level of the plurality of spinal levels:
employing volumetric fiducial points associated with said each spinal level and corresponding intraoperative fiducial points associated with said each spinal level to perform an initial registration between the segmented surface data associated with said each spinal level and the intraoperative surface data, and subsequently performing a surface-to-surface registration between the segmented surface data associated with said each spinal level and the intraoperative surface data, thereby obtaining a registration transform associated with said each spinal level; and
employing the registration transforms associated with the plurality of spinal levels to generate measures associated with an intraoperative spinal orientation, and providing feedback based on the measures.

* * * * *